United States Patent
Mohanty et al.

(10) Patent No.: US 11,548,920 B2
(45) Date of Patent: Jan. 10, 2023

(54) METHOD, COMPOSITIONS AND APPLICATIONS OF MECHANOSENSITIVE CHANNELS IN VISUAL DISORDERS AND OTHER APPLICATIONS THEREOF

(71) Applicant: Nanoscope Technologies LLC, Bedford, TX (US)

(72) Inventors: Samarendra Kumar Mohanty, Arlington, TX (US); Chinenye Abiodun Idigo, Mansfield, TX (US)

(73) Assignee: Nanoscope Technologies, LLC, Bedford, TX (US)

( * ) Notice: Subject to any disclaimer, the term of this patent is extended or adjusted under 35 U.S.C. 154(b) by 0 days.

(21) Appl. No.: 17/419,878

(22) PCT Filed: Dec. 30, 2019

(86) PCT No.: PCT/US2019/068912
§ 371 (c)(1),
(2) Date: Jun. 30, 2021

(87) PCT Pub. No.: WO2020/142415
PCT Pub. Date: Jul. 9, 2020

(65) Prior Publication Data
US 2022/0048956 A1    Feb. 17, 2022

Related U.S. Application Data

(60) Provisional application No. 62/786,955, filed on Dec. 31, 2018.

(51) Int. Cl.
*C07K 14/245* (2006.01)
(52) U.S. Cl.
CPC ................. *C07K 14/245* (2013.01)
(58) Field of Classification Search
None
See application file for complete search history.

(56) References Cited

U.S. PATENT DOCUMENTS

2012/0034619 A1   2/2012 Walton et al.

OTHER PUBLICATIONS

Doerner, Julia F., et al.; Controlled delivery of bioactive molecules into live cells using the bacterial mechanosensitive channel MscL; Nature Communications 3:990; Aug. 7, 2012.
Genbank Accession ML Y52435.1, large-conductance mechanosensitive channel protein MscL [*Escherichia aibertii*]; Publication [online], Dec. 7, 2018 [retrieved Apr. 6, 2020], Retrieved from the Internet: ; pp. 1-2.
Heureaux-Torres, JL. Bacterial Mechanosensitive Channel of Large Conductance (MscL) in Mammalian Cells for Novel Mechanobiology Applications. Dissertation. University of Michigan. Publication (online) Jun. 7, 2018 (retrieved Apr. 6, 2020). Retrieved from the Internet ; p. 11, second paragraph; p. 52, third paragraph; p. 54, second paragraph.
International Search Report, PCT/US2019/068912.
Written Opinion, PCT/US2019/068912.
"Large conductance mechanosensitive channel protein [*Escherichiacoli* HS]" [Jan. 31, 2014] Retrieved from GenBank [online] Accession No. ABV07699.1 [retrieved on Nov. 29, 2021] URL: [http/www.nebi.nlm.nih.gov/protein/ABV07699.1/].
Li, Xiao-Fang et. al. "Molecular Cloning of a Fourth Member of the Potassium-dependent Sodium-Calcium Exchanger Gene Family, NCKX4" J. Biol. Chem. (2002) 277(50):48410-48417.

*Primary Examiner* — Suzanne M Noakes
(74) *Attorney, Agent, or Firm* — Shirley A. Recipon

(57) ABSTRACT

Some embodiments of the present invention generally relate to the novel method, compositions and applications of mechanosensitive channels in therapeutics for visual, neurological and other disorders. Specifically, some embodiments of the invention relate to exploitation of mechanosensitive channels' intrinsic property as a transgenic pressure modulator and alternative outflow actuator in the treatment of different diseases such as glaucoma, dry eye disease and other diseases involving of cells prone to mechanical or osmotic stress. Furthermore, some embodiments of the invention relate to exploitation of mechanosensitive channels for stimulation of cells as well as molecular delivery to cells triggered by internal as well as external mechanical stimuli.

25 Claims, 8 Drawing Sheets
(7 of 8 Drawing Sheet(s) Filed in Color)
Specification includes a Sequence Listing.

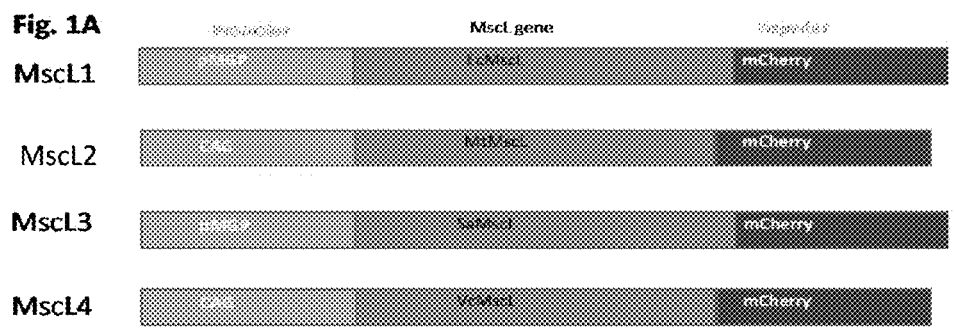
Fig. 1A
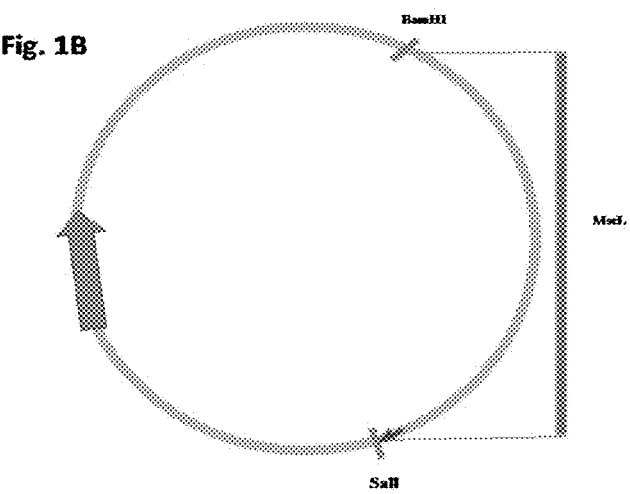
Fig. 1B
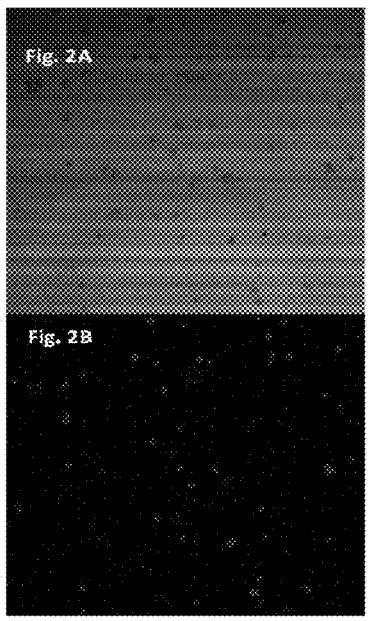
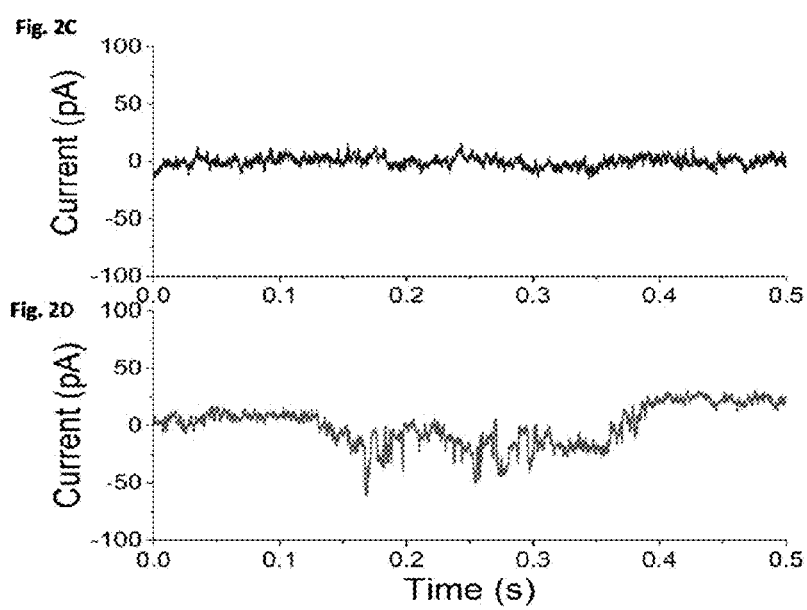

Fig. 5A
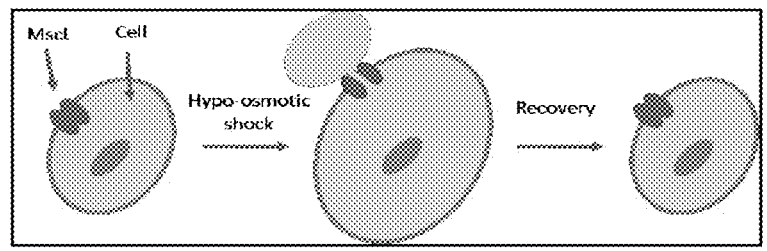
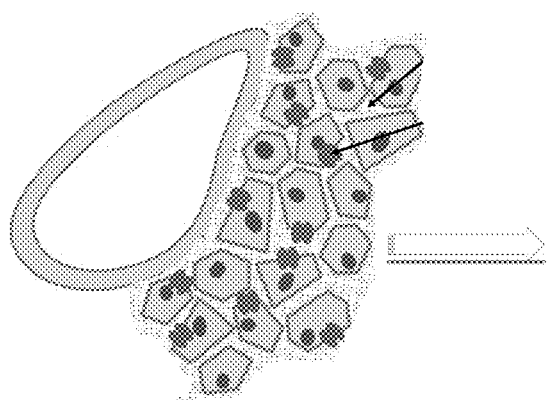
Fig. 6A
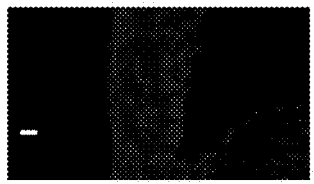
Fig. 6B
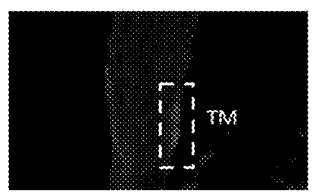
Fig. 6D
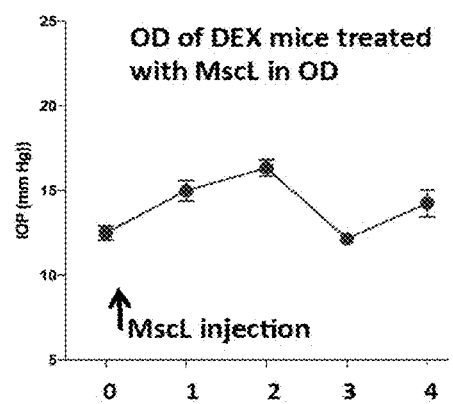
Fig. 6C
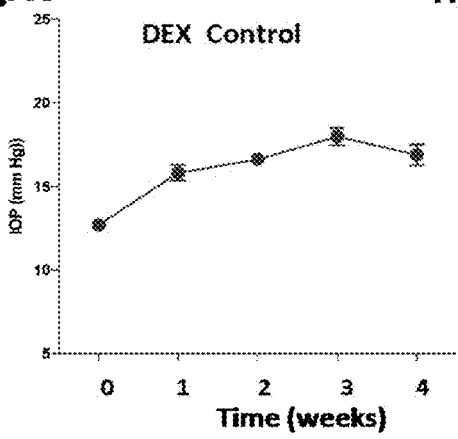
Fig. 6E
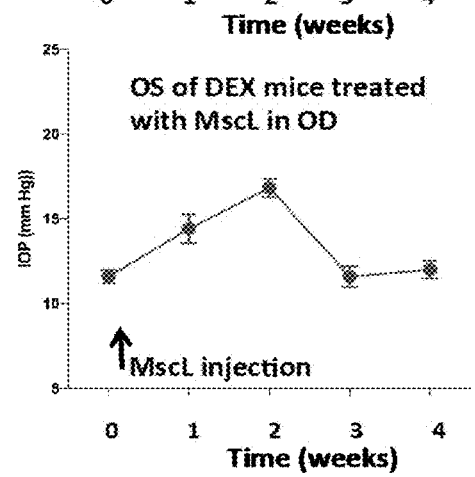

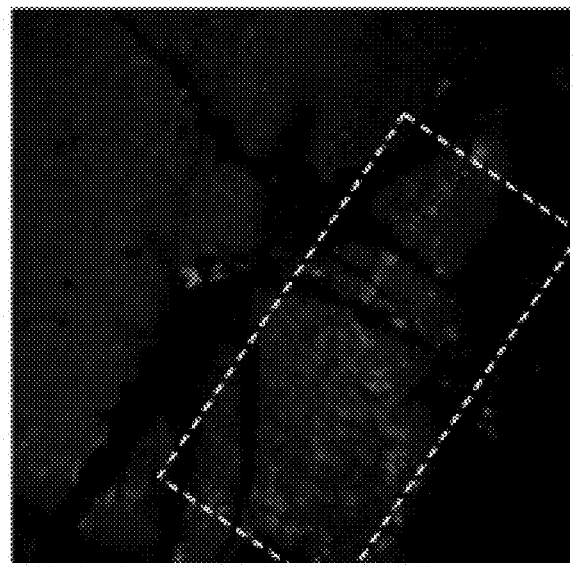
Fig. 7
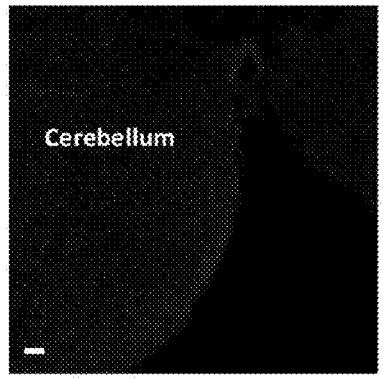
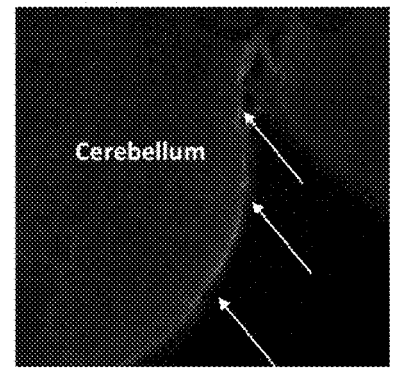
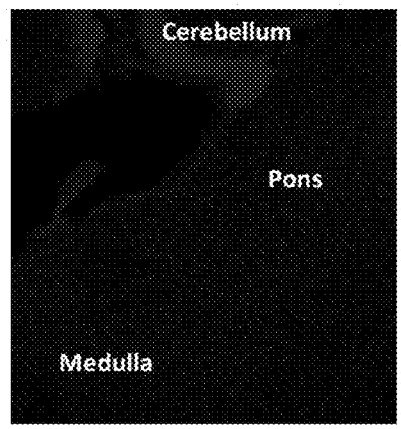
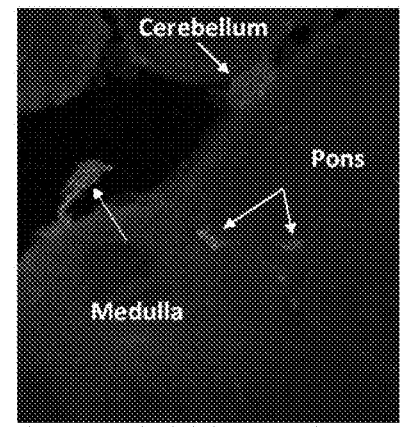

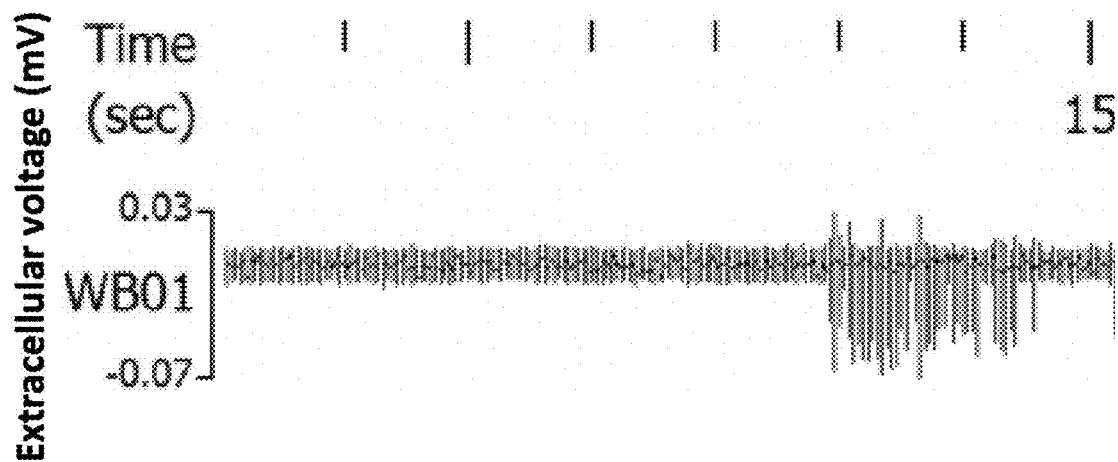
Fig. 13
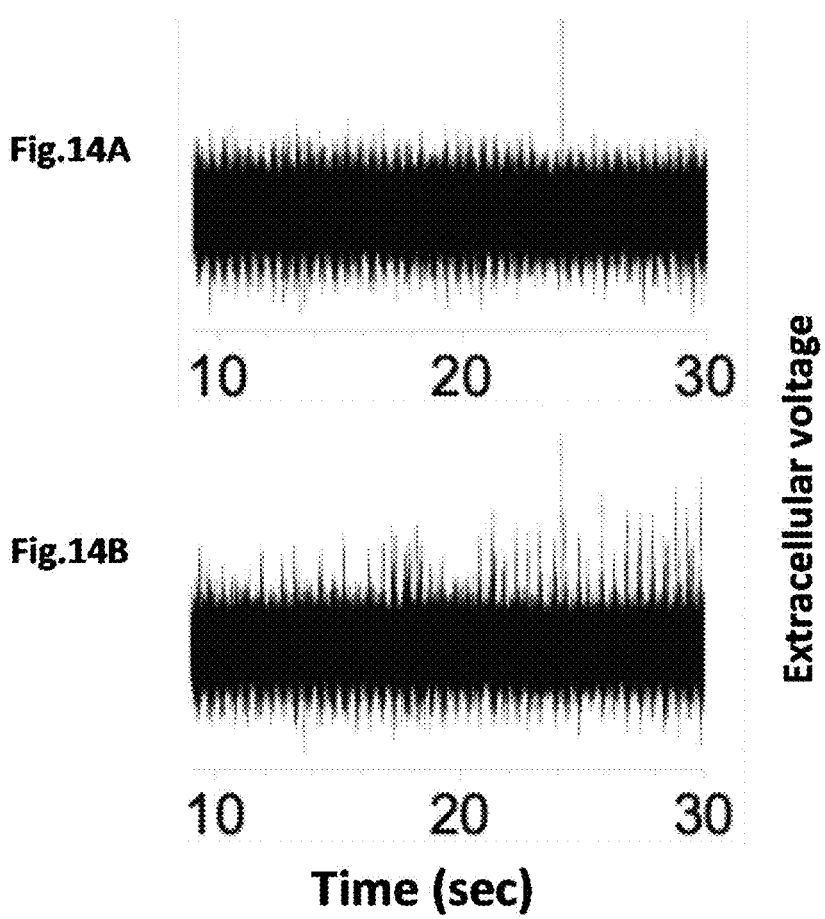
Fig.14A
Fig.14B

SEQUENCE LISTING

```
<160> NUMBER OF SEQ ID NOS: 9

<210> SEQ ID NO 1
<211> LENGTH: 157
<212> TYPE: PRT
<213> ORGANISM: Artificial Sequence
<220> FEATURE:
<223> OTHER INFORMATION: Synthetic Peptide

<400> SEQUENCE: 1

Met Leu Pro Gln Gln Val Gly Phe Val Cys Ala Val Leu Ala Leu Val
1               5                   10                  15

Cys Cys Ala Ser Gly Met Ser Ile Ile Lys Glu Phe Arg Glu Phe Ala
            20                  25                  30

Met Arg Gly Asn Val Val Asp Leu Ala Val Gly Val Ile Ile Gly Ala
        35                  40                  45
```

Ala Phe Gly Lys Ile Val Ser Ser Leu Val Ala Asp Ile Ile Met Pro
 50                  55                  60

Pro Leu Gly Leu Leu Ile Gly Gly Ile Asp Phe Lys Gln Phe Ala Val
 65                  70                  75                  80

Thr Leu Arg Asp Ala Gln Gly Asp Ile Pro Ala Val Val Met His Tyr
                 85                  90                  95

Gly Val Phe Ile Gln Asn Val Phe Asp Phe Leu Ile Val Ala Phe Ala
                100                 105                 110

Ile Phe Met Ala Ile Lys Leu Ile Asn Lys Leu Asn Arg Lys Lys Glu
            115                 120                 125

Glu Pro Ala Ala Ala Pro Ala Pro Thr Lys Glu Glu Val Leu Leu Thr
130                 135                 140

Glu Ile Arg Asp Leu Leu Lys Glu Gln Asn Asn Arg Ser
145                 150                 155

<210> SEQ ID NO 2
<211> LENGTH: 172
<212> TYPE: PRT
<213> ORGANISM: Artificial Sequence
<220> FEATURE:
<223> OTHER INFORMATION: Synthetic Peptide

<400> SEQUENCE: 2

Met Leu Pro Gln Gln Val Gly Phe Val Cys Ala Val Leu Ala Leu Val
 1                   5                  10                  15

Cys Cys Ala Ser Gly Met Leu Lys Gly Phe Lys Glu Phe Leu Ala Arg
                20                  25                  30

Gly Asn Ile Val Asp Leu Ala Val Ala Val Ile Gly Thr Ala Phe Thr
                35                  40                  45

Thr Ala Leu Val Thr Lys Phe Thr Asp Ser Ile Ile Thr Pro Leu Ile
 50                  55                  60

Asn Arg Ile Gly Val Asn Ala Gln Ser Asp Val Gly Ile Leu Arg Ile
 65                  70                  75                  80

Gly Ile Gly Gly Gly Gln Thr Ile Asp Leu Asn Val Leu Leu Ser Ala
                85                  90                  95

Ala Ile Asn Phe Phe Leu Ile Ala Phe Ala Val Tyr Phe Leu Val Val
                100                 105                 110

Leu Pro Tyr Asn Thr Leu Arg Lys Lys Gly Glu Val Glu Gln Pro Gly
            115                 120                 125

Asp Thr Gln Val Val Leu Leu Thr Glu Ile Arg Asp Leu Leu Ala Gln
130                 135                 140

Thr Asn Gly Asp Ser Pro Gly Arg His Gly Gly Arg Gly Thr Pro Ser
145                 150                 155                 160

Pro Thr Asp Gly Pro Arg Ala Ser Thr Glu Ser Gln
                165                 170

<210> SEQ ID NO 3
<211> LENGTH: 141
<212> TYPE: PRT
<213> ORGANISM: Artificial Sequence
<220> FEATURE:
<223> OTHER INFORMATION: Synthetic Peptide

<400> SEQUENCE: 3

Met Leu Pro Gln Gln Val Gly Phe Val Cys Ala Val Leu Ala Leu Val
 1                   5                  10                  15

Cys Cys Ala Ser Gly Met Leu Lys Glu Phe Lys Glu Phe Ala Leu Lys
                20                  25                  30

Gly Asn Val Leu Asp Leu Ala Ile Ala Val Val Met Gly Ala Ala Phe
            35                  40                  45

Asn Lys Ile Ile Ser Ser Leu Val Glu Asn Ile Ile Met Pro Leu Ile
 50                  55                  60

Gly Lys Ile Phe Gly Ser Val Asp Phe Ala Lys Glu Trp Ser Phe Trp
 65                  70                  75                  80

Gly Ile Lys Tyr Gly Leu Phe Ile Gln Ser Val Ile Asp Phe Ile Ile
                 85                  90                  95

Ile Ala Phe Ala Leu Phe Ile Phe Val Lys Ile Ala Asn Thr Leu Met
                100                 105                 110

Lys Lys Glu Glu Ala Glu Glu Ala Val Val Glu Glu Asn Val Val
                115                 120                 125

Leu Leu Thr Glu Ile Arg Asp Leu Leu Arg Glu Lys Lys
            130                 135                 140

<210> SEQ ID NO 4
<211> LENGTH: 157
<212> TYPE: PRT
<213> ORGANISM: Artificial Sequence
<220> FEATURE:
<223> OTHER INFORMATION: Synthetic Peptide

<400> SEQUENCE: 4

Met Leu Pro Gln Gln Val Gly Phe Val Cys Ala Val Leu Ala Leu Val
 1               5                  10                  15

Cys Cys Ala Ser Gly Met Ser Leu Leu Lys Glu Phe Lys Ala Phe Ala
                20                  25                  30

Ser Arg Gly Asn Val Ile Asp Met Ala Val Gly Ile Ile Ile Gly Ala
            35                  40                  45

Ala Phe Gly Lys Ile Val Ser Ser Phe Val Ala Asp Ile Ile Met Pro
 50                  55                  60

Pro Ile Gly Ile Ile Leu Gly Gly Val Asn Phe Ser Asp Leu Ser Phe
 65                  70                  75                  80

Val Leu Leu Ala Ala Gln Gly Asp Ala Pro Ala Val Val Ile Ala Tyr
                 85                  90                  95

Gly Lys Phe Ile Gln Thr Val Val Asp Phe Thr Ile Ile Ala Phe Ala
                100                 105                 110

Ile Phe Met Gly Leu Lys Ala Ile Asn Ser Leu Lys Arg Lys Glu Glu
                115                 120                 125

Glu Ala Pro Lys Ala Pro Pro Ala Pro Thr Lys Asp Gln Glu Leu Leu
                130                 135                 140

Ser Glu Ile Arg Asp Leu Leu Lys Ala Gln Gln Asp Lys
145                 150                 155

<210> SEQ ID NO 5
<211> LENGTH: 157
<212> TYPE: PRT
<213> ORGANISM: Artificial Sequence
<220> FEATURE:
<223> OTHER INFORMATION: Synthetic Peptide

<400> SEQUENCE: 5

Met Leu Pro Gln Gln Val Gly Phe Val Cys Ala Val Leu Ala Leu Val
 1               5                  10                  15

Cys Cys Ala Ser Gly Met Ser Ile Ile Lys Glu Phe Arg Glu Phe Ala
                20                  25                  30

Met Arg Gly Asn Val Val Asp Leu Ala Val Gly Val Ile Ile Gly Ala

```
                35                   40                  45
Ala Phe Gly Lys Ile Val Ser Ser Leu Val Ala Asp Ile Ile Met Pro
             50                  55                  60

Pro Leu Gly Leu Leu Glu Gly Ile Asp Phe Lys Gln Phe Ala Val
 65                  70                  75                  80

Thr Leu Arg Asp Ala Gln Gly Asp Ile Pro Ala Val Val Met His Tyr
                 85                  90                  95

Gly Val Phe Ile Gln Asn Val Phe Asp Phe Leu Ile Val Ala Phe Ala
                100                 105                 110

Leu Phe Met Ala Ile Lys Leu Ile Asn Lys Leu Asn Arg Lys Lys Glu
                115                 120                 125

Glu Pro Ala Ala Ala Pro Ala Pro Thr Lys Glu Glu Val Leu Leu Thr
            130                 135                 140

Glu Ile Arg Asp Leu Leu Lys Glu Gln Asn Asn Arg Ser
145                 150                 155

<210> SEQ ID NO 6
<211> LENGTH: 157
<212> TYPE: PRT
<213> ORGANISM: Artificial Sequence
<220> FEATURE:
<223> OTHER INFORMATION: Synthetic Peptide

<400> SEQUENCE: 6

Met Leu Pro Gln Gln Val Gly Phe Val Cys Ala Val Leu Ala Leu Val
 1               5                  10                  15

Cys Cys Ala Ser Gly Met Ser Ile Ile Lys Glu Phe Arg Glu Phe Ala
             20                  25                  30

Met Arg Gly Asn Val Val Asp Leu Ala Val Gly Val Ile Ile Gly Ala
             35                  40                  45

Ala Phe Gly Lys Ile Val Ser Ser Leu Val Ala Asp Ile Ile Met Pro
         50                  55                  60

Pro Leu Gly Leu Leu Ile Gly Gly Ile Asp Phe Lys Gln Phe Ala Val
 65                  70                  75                  80

Thr Leu Arg Asp Ala Gln Gly Asp Ile Pro Ala Val Val Met His Tyr
                 85                  90                  95

Gly Val Phe Ile Gln Asn Val Phe Asp Phe Leu Ile Val Ala Phe Ala
                100                 105                 110

Leu Phe Met Ala Ile Lys Leu Ile Asn Thr Leu Asn Arg Lys Lys Glu
                115                 120                 125

Glu Pro Ala Ala Ala Pro Ala Pro Thr Lys Glu Glu Val Leu Leu Thr
            130                 135                 140

Glu Ile Arg Asp Leu Leu Lys Glu Gln Asn Asn Arg Ser
145                 150                 155

<210> SEQ ID NO 7
<211> LENGTH: 21
<212> TYPE: PRT
<213> ORGANISM: Artificial Sequence
<220> FEATURE:
<223> OTHER INFORMATION: Synthetic Peptide

<400> SEQUENCE: 7

Met Leu Pro Gln Gln Val Gly Phe Val Cys Ala Val Leu Ala Leu Val
 1               5                  10                  15

Cys Cys Ala Ser Gly
             20
```

```
<210> SEQ ID NO 8
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 8

Met Gly Arg Leu Leu Ala Leu Val Val Gly Ala Ala Leu Val Ser Ser
1               5                   10                  15

Ala Cys

<210> SEQ ID NO 9
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 9

Met Ala Val Pro Ala Arg Thr Cys Gly Ala Ser Arg Pro Gly Pro Ala
1               5                   10                  15

Arg Thr
```

METHOD, COMPOSITIONS AND APPLICATIONS OF MECHANOSENSITIVE CHANNELS IN VISUAL DISORDERS AND OTHER APPLICATIONS THEREOF

CROSS-REFERENCE

This application claims the benefit of U.S. provisional application No. 62/786,955 filed Dec. 31, 2018, which application is incorporated herein by reference.

Some references, which may include publications, patents, and patent applications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference were individually incorporated by reference.

DESCRIPTION OF THE TEXT FILE SUBMITTED ELECTRONICALLY

The contents of the text field submitted electronically herewith are incorporated herein by reference in their entirety: A computer readable format copy of the Sequence Listing (file name: CHINENYE_SL_2019.txt, date recorded: Dec. 4, 2019, file size 9 kilobytes), which was replaced by computer readable format copy of the Sequence Listing on Jun. 10, 2022 (file name: Chinyenye SL revised Jun2022.txt, date recorded: Jun. 10, 2022, file size 10 kilobytes).

FIELD OF INVENTION

The present invention generally relates to the novel method, compositions and applications of mechanosensitive channels in therapies of different disorders of the eye and other organs. Specifically, the invention relates to exploitation of mechanosensitive channels of large conductance (MscL)'s intrinsic property as a transgenic pressure modulator and alternative outflow actuator in the treatment of glaucoma, dry-eye and other diseases involving cells prone to mechanical or osmotic stress. Furthermore, the invention relates to exploitation of mechanosensitive channels for molecular delivery triggered by internal as well as external mechanical stimuli.

BACKGROUND OF INVENTION

Cells of different organs in the body undergoes range of mechanical and osmotic pressures which changes in various diseases including neurological, cardiovascular, ophthalmological, and renal diseases. While, in bacteria, the mechanosensitive channel of large conductance (MscL) functions as an osmoregulator and protects cells from lysis upon hypo-osmotic shock, such channels are not present in mammalian cells.

As an example of a targeted pressure-related disorder, vision loss due to glaucoma is the second leading cause of blindness in America[1]. The livelihood, independence and quality of life of millions of glaucoma patients and their families are being disrupted by this pervasive disease.

Glaucoma is defined as a group of eye conditions, which cause damage to the optic nerve usually due to elevated intraocular pressure (IOP). The most common form of glaucoma is primary open angle glaucoma (POAG) and it is characterized by poor drainage of aqueous humor through the conventional outflow pathway. In the conventional outflow pathway, aqueous humor drains through the trabecular meshwork (TM), into Schlemm's canal and on into the episcleral vein. Several studies have characterized distinct changes in TM cellular processes and proteinaceous structures in glaucomatous eyes, which purportedly account for increased (TM) stiffness and aqueous humor outflow resistance[2].

The eye must maintain a healthy internal pressure to preserve its form and function. A healthy intraocular pressure (IOP) is maintained by continuous upkeep of vitreous and aqueous humor processing. Aqueous humor is responsible for the structure, nutrition and hygiene of the tissues in the anterior chamber and proper regulation of its inflow and outflow balance is critical. Aqueous humor is produced by the ciliary body, flows through the pupil and drains out through either the conventional outflow pathway or the uveoscleral pathway. In the conventional outflow pathway aqueous humor flows through the trabecular meshwork (TM), into Schlemm's canal, and out into episcleral blood vessels through ducts that branch out of the canal. Glaucoma is defined as a group of eye conditions which cause damage to the optic nerve, usually due to elevated IOP. There are four main avenues by which IOP can be decreased; i) reduce aqueous humor production, ii) increase outflow through the uveoscleral pathway, iii) improve drainage through the conventional pathway, or iv) create an alternate outflow pathway.

The currently available pharmacological and surgical treatments for glaucoma have significant limitations and side effects. These undesirable side effects include, systemic reactions to medications, patient non-compliance, eye infections, surgical device failure, and damage to other structures of the eye. To forestall disease progression, most glaucoma cases will need multiple medical interventions over time. For example, even after surgery some glaucoma patients will still need to take daily eyedrops for an indefinite period. The development of a safe effective long-lasting single-dose therapeutic for the ubiquitous treatment of glaucoma.

The other treatment option for uncontrollable glaucoma is surgery. The most common glaucoma surgery is a trabeculectomy, where an alternative outflow pathway is created by removing a section of the sclera, Schlemm's canal and TM and fashioning a filtration bleb out of a conjunctival tissue flap. Other surgical methods include, canaloplasty, laser trabeculoplasty, laser peripheral iridotomy, deep non-perforating sclerectomy, and drainage device implantation. As with all surgeries, there are risks of infection, systemic side effects and human/device failure. Post-surgical scarring at the procedure site is common and scar tissue can block or shift the newly created drainage pathway. With the added considerations of the expense, patient recovery time and inconsistent outcomes of surgery, it becomes clear that new and innovative treatments for glaucoma are needed.

SUMMARY OF THE INVENTION

To address the above-mentioned challenges, the present invention provides novel methods, compositions and applications of heterologously expressed mechanosensitive channels as tension activated pressure release valves in mammalian cells including trabeculocytes and epithelial cells.

In bacteria, the mechanosensitive channel of large conductance (MscL) functions as an osmoregulator and protects cells from lysis upon hypo-osmotic shock. The MscL directly senses tension in the membrane lipid bilayer of the swelling cell and in response transiently opens its large non-specific pore to release cytoplasmic fluid, thereby relieving the building turgor pressure.

In an aspect of the invention, the present invention describes a method to use MscL as a virally delivered transgenic pressure modulator in the impaired TM cells of glaucomatous eyes.

In an embodiment of the invention, the present invention describes a synthetic polypeptide sequence of MscL1 protein and its generated site-directed mutants comprising: An MscL1 protein (SEQ ID NO: 1) that, when expressed on mammalian cell membrane, senses pressure changes and modulates the intra-cellular pressure, or molecular transport not limited to aqueous fluid and therapeutic molecules.

In another embodiment of the invention, the present invention describes a protein, wherein one or more of a single or combination of mutations modulate pressure sensitivity, pore size, gating, or kinetics. For example, present invention demonstrates I to L substitution at an amino acid residue corresponding to amino acid I at 113 position of the MscL sequence SEQ ID No. 1 to sensitize the cells toward ultrasound activation at very low pressure. Furthermore, hypersensitivity to stretch forces (activated at far below the threshold for MscS), increase in pressure sensitivity is achieved by G to Any other 19 naturally occurring amino acid substitution at an amino acid residue corresponding to amino acid G at 43 position of the MscL sequence ID No. 1.

In another embodiment, the present invention describes a protein, wherein to increase the pressure sensitivity and shorten the open times, V to C amino acid substitution at an amino acid residue corresponding to amino acid V at 44 position of the MscL sequence ID No. 1 is carried out. Increased the pressure sensitivity and shorter open times is also achieved by deletion of amino acid(s) from 131 to 133, 131 to 136 or 131 to 157 position(s) of the MscL sequence ID No 1.

In another embodiment of the invention, present invention demonstrates increased pressure sensitivity of the protein (sequence ID No. 1) by substitution of K at 122 position to any negatively charged amino acid at an amino acid residue. Furthermore, substitution of K at 52 position of the MscL sequence ID No. 1 leads to increased pressure sensitivity and shorter mean open times, lower transition barrier. Q to C or P or F or W or Y or H amino acid substitution at an amino acid residue corresponding to amino acid Q at 77 position of the MscL sequence ID No. 1 leads to increased pressure sensitivity and increased mean open time, high transition barrier. In addition, L to C amino acid substitution at an amino acid residue corresponding to amino acid L at 40 position of the MscL sequence ID No. 1 results in sensitiveness to higher gating threshold.

In another embodiment of the invention, the present invention describes a synthetic polypeptide sequence of MscL2 protein (SEQ ID NO: 2) and its generated site-directed mutants The MscL2 protein when expressed on mammalian cell membrane, senses pressure changes and modulate the intra-cellular pressure, or molecular transport not limited to aqueous fluid and therapeutic molecules.

In another embodiment of the invention, the present invention describes a synthetic polypeptide sequence of MscL3 protein and its generated site-directed mutants. The MscL3 protein (SEQ ID NO: 3) that, when expressed on mammalian cell membrane, senses pressure changes and modulate the intra-cellular pressure, or molecular transport not limited to aqueous fluid and therapeutic molecules.

In another embodiment of the invention, the present invention describes a synthetic polypeptide sequence of MscL4 protein and its generated site-directed mutants comprising: An MscL4 protein (SEQ ID NO: 4) that, when expressed on mammalian cell membrane, senses pressure changes and modulate the intra-cellular pressure, or molecular transport not limited to aqueous fluid and therapeutic molecules.

In another embodiment of the invention, the present invention describes a synthetic polypeptide sequence wherein one or more of MscL protein(s) or chimera of sequence elements of different MscL protein(s) or concatemers of MscL monomers expressed in a cell is fused to one or more amino acid sequence motifs selected from the group consisting of a signal peptide, an endoplasmic reticulum (ER) export signal, a membrane trafficking signal, and an N-terminal Golgi export signal. Specifically, the signal consists of SEQ ID NO: 7 (MLPQQVGFVCAVLALVCCASG). The signaling sequence can also be selected from SEQ ID NO: 8 (MGRLLALVVGAALVSSAC) or SEQ ID NO: 9 (MAVPARTCGASRPGPART) or any signaling peptide sequences.

In another embodiment of the invention, the present invention describes a method wherein heterologously expressed mechanosensitive channels, such as bacterial mechanosensitive channels (MscL, MscS, MscK, MscG), plant mechanosensitive channels (MSL2-10), TRPV1-TRPV5 channels, Piezo channels or their generated site-directed mutants are used as a tension activated pressure release valve in cells including trabeculocytes, epithelial cells and other cells of the body that are subjected to mechanical or osmotic pressure for therapeutic purpose.

In another embodiment of the invention, the present invention describes a method and compositions, wherein the MscL homologues strains include but not limited to bacterial, fungi, yeast etc.

In yet another embodiment, the present invention describes the compositions, wherein the Mscl homologues strains includes but not limited to MscLs from *Escherichia coli, Mycobacterium Tuberculosis, Vibrio cholera, Bacillus subtilis, Mycobacterium leprae, Chlorobium tepidum, Thermus thermophilus, Haemophilus influenza, Erwinia carotovora, Pseudomonas fluorescens, Clostridium perfringens, Staphylococcus aureus, Streptococcus faecalis, Lactococcus lactis, Brucella melitensis, Caulobacter crescentus, Clostridium histolyticum, Fusobacterium nucleatum* subsp, *Mesorhizobium loti, Pasteurella multocida, Pectobacterium carotovorum, Pseudomonas aeruginosa, Salmonella enterica serovar Typhimurium, Salmonella enterica serovar Typhi, Xylella fastidiosa, Corynebacterium glutamicum, Deinococcus radiodurans, Lactococcus lactis, Ralstonia solanacearum, Sinorhizobium meliloti, Streptococcus pneumoniae, Streptococcus pyogenes, Streptomyces coelicolor, Methanosarcina acetivorans Listeria innocua, Listeria monocytogenes* etc.

In another embodiment, this invention provides a method wherein MscL would function as an alternative outflow actuator for the treatment of POAG.

In another embodiment, this invention provides a method, wherein MscL function would supplement native paracytosis and transcytosis in the movement of aqueous humor around and through the endothelial cells of the TM, thereby alleviating outflow resistance and lowering of IOP for the treatment of POAG (Primary open angle glaucoma)

In yet another embodiment of the invention, the present invention describes a method wherein the said mechanosensitive channel (e.g., MscL) is delivered through viral vectors (e.g., adeno virus, adeno associated-virus, lentivirus) or non-viral methods and said channel acts as a transgenic pressure modulator in the impaired cells of glaucomatous eyes in selected but not limited to Trabecular Meshwork (TM) cells by use of promoters such as matrix Gla protein (MGP) promoter.

In another embodiment of the invention, the present invention describes non-viral methods (lipofection, nanoparticle/laser-mediated delivery) for delivery of the mechanosensitive channel encoding genes to the targeted tissue.

Another aspect of this invention describes the application of MscL as an ideal candidate to use as a drainage valve in trabeculocytes because it is a relatively small homo-oligomeric channel and does not need any associated proteins or energy sources to assemble and function.

In yet another embodiment, this invention provides a method wherein, the said mechanosensitive channel, its variants, and the generated site-directed mutants are activated at selected but not limited to physiological and non-physiological pressures such as greater than 20 mmHg in eye; or 120-200 mmHg (systolic) and 80-110 (diastolic) in artery; or greater than 15 mmHg intracranial pressure.

In a specific embodiment, this invention demonstrates delivery and expression of MscL in the cells of trabecular meshwork (TM). The MscL microbial channel would function in the foreign environment of the TM and lead towards lowering of IOP in glaucoma patients.

In yet another embodiment, this invention provides a method wherein the expression of the said mechanosensitive channel in meibomian glands endothelial cells, corneal epithelial cells etc with or without mechanical stimulation would lead to enhanced secretion of aqueous phase of the tear film and thus, alleviation of dry eye disease (DED).

In yet another embodiment, this invention provides a method wherein, MscL, or its variants, or generated site-directed mutants, when expressed in mammalian cells, can be used for molecular delivery into the cells by application of extra-cellular stimuli including osmotic stress or other mechanical actuation not limiting to ultrasound and hydrodynamic pressure.

In yet another embodiment, this invention provides a method wherein, MscL, or its variants, or generated site-directed mutants, when expressed in mammalian cells, can be used for stimulation of the cells by application of extra-cellular stimuli not limiting to ultrasound modulation.

In a broader embodiment, this invention provides a composition and method wherein MscL or its variants, or generated site-directed mutants, delivered via viral or non-viral (physical, chemical) method, expressed in targeted mammalian cells in a promoter-specific manner, the microbial channel(s) would function in the foreign environment under specific range of mechanical stimuli or osmotic stress generated inside the body or externally using specific device not limiting to ultrasound modulation.

It is contemplated that any embodiment of a method, device or composition described herein can be implemented with respect to any other method, device or composition described herein.

In one aspect, the amino acid has at least one of 75%, 85%, 95% or 100% identity to SEQ ID NO: 1, 2, 3, 4, 5 or 6.

Details associated with the embodiments described above and others are described below.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings illustrate by way of example and not limitation. For the sake of brevity and clarity, every feature of a given structure is not always labeled in every figure in which that structure appears. The following drawings form part of the present specification and are included to further demonstrate certain aspects of the present invention. The invention may be better understood by reference to one or more of these drawings in combination with the detailed description of the specification embodiments presented herein.

Tables 1-6 show Amino acid sequences of different MscLs: MscL1, MscL2, MscL3, and MscL4. Different promoters (e.g., pMGP, CAG) are used upstream of MscL-sequences for targeting specific cells as an example.

FIG. 1A. Typical domain architecture of MscL gene constructs with 5' promoter sequences and 3' fluorescent (mCherry) reporter sequences. FIG. 1B. Typical circular DNA plasmid map showing the insertion of MscL gene construct cloned between two restriction sites (BamH I and Sal I).

FIG. 2A. Bright field image of HEK293 cells transfected with plasmid DNA containing the EcMscL-mCherry gene. FIG. 2B. Red filtered confocal fluorescence image of HEK293 cells transfected with plasmid DNA containing the EcMscL-mCherry gene. 488 nm excitation and 560-660 nm emission filter. FIG. 2C. Stable current profile of an EcMscL expressing HEK293 cell before hypotonic shock. FIG. 2D. Inward current profile of an EcMscL expressing HEK293 cell in response to hypotonic shock (addition of 20% v/v water).

Figure 3A:
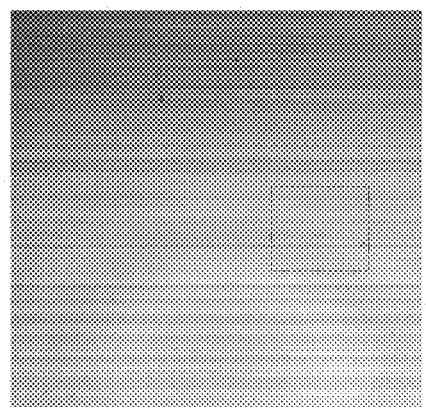
Figure 3B:
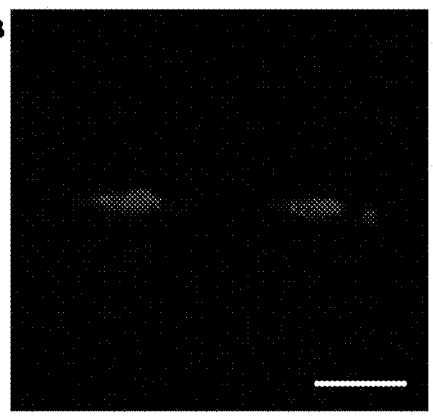
Figure 3C:
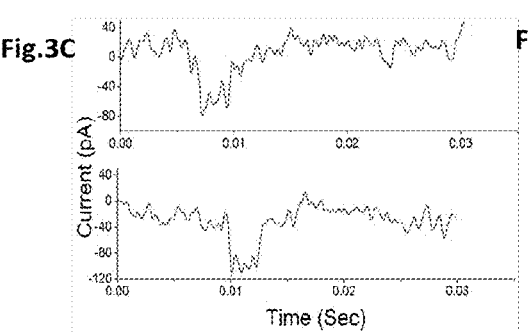
Figure 3D:
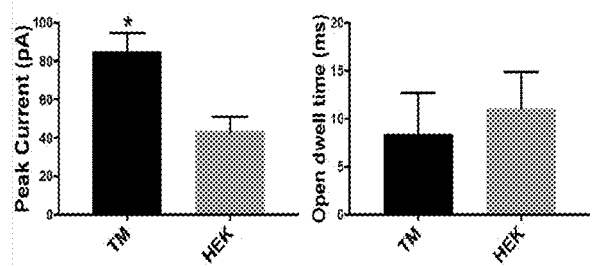

FIG. 3A. Composite of bright field and red filtered confocal fluorescence images of embryonic rat trabecular meshwork cells transfected with plasmid DNA containing the EcMscL-mCherry gene. FIG. 3B. Zoomed confocal fluorescence (560-660 nm emission) image of two embryonic rat trabecular meshwork cells transfected with plasmid DNA containing the EcMscL-mCherry gene. FIG. 3C. Inward current profile of an EcMscL expressing rat TM cell in response to hypotonic shock (addition of ~20$% v/v water). FIG. 3D. Comparison of EcMscL channel peak current and open dwell times in TM and HEK cells. N=5, AV±S.D. *p<0.001.

Figure 4A:
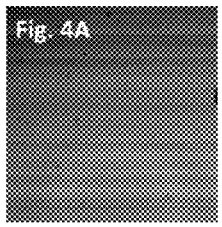
Figure 4D:
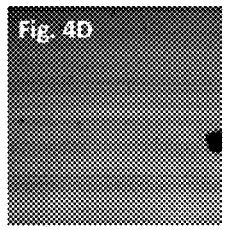
Figure 4G:
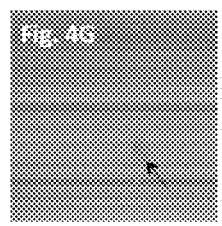
Figure 4J:
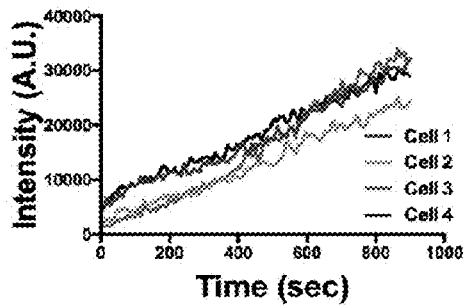
Figure 4B:
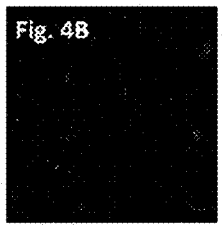
Figure 4E:
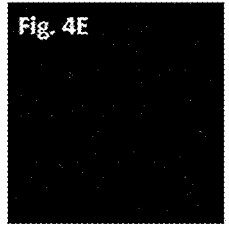
Figure 4H:
Figure 4C:
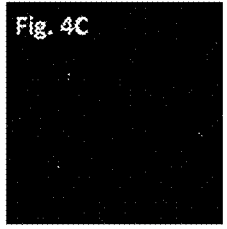
Figure 4F:
Figure 4I:
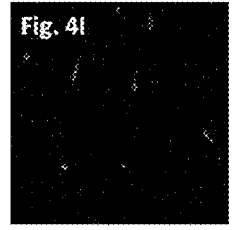

FIG. 4A. Bright field image of embryonic rat trabecular meshwork cells transfected with plasmid DNA containing the EcMscL-mCherry gene. FIG. 4B. Confocal fluorescence (560-660 nm emission) image of embryonic rat trabecular meshwork cells transfected with plasmid DNA containing the EcMscL-mCherry gene. FIG. 4C. Confocal fluorescence (488 nm excitation and 505-525 nm emission) image of embryonic rat trabecular meshwork cells transfected with plasmid DNA containing the EcMscL-mCherry gene. FIG. 4D. Bright field image of embryonic rat trabecular meshwork cells, transfected with plasmid DNA containing the EcMscL-mCherry gene, in ~1 U/mL Alexa Fluor™ 488 Phalloidin dye. FIG. 4E. Confocal fluorescence (488 nm excitation and 505-525 nm emission) image of embryonic rat trabecular meshwork cells, transfected with plasmid DNA containing the EcMscL-mCherry gene, in ~1 U/mL Alexa Fluor™ 488 Phalloidin dye. FIG. 4F. Confocal fluorescence (488 nm excitation and 505-525 nm emission) image of embryonic rat trabecular meshwork cells, transfected with plasmid DNA containing the EcMscL-mCherry gene, in ~2 U/mL Alexa Fluor™ 488 Phalloidin dye. FIG. 4G. Bright field image of embryonic rat trabecular meshwork cells, transfected with plasmid DNA containing the EcMscL-mCherry gene, in ~2 U/mL Alexa Fluor™ 488 Phalloidin dye. 15 minutes after a hypo-osmotic shock (addition of 20% v/v water). The control (not expressing EcMscL-mCherry) is marked by arrow. FIG. 4H. Confocal fluorescence (488 nm excitation and 505-525 nm emission) image of embryonic rat trabecular meshwork cells, transfected with plasmid DNA containing the EcMscL-mCherry gene, in ~2 U/mL Alexa Fluor™ 488 Phalloidin dye. 7.5 minutes after a hypo-osmotic shock (addition of 20% v/v water). 488 nm excitation and 505-525 nm emission filter. FIG. 4I. Green filtered confocal fluorescence image of embryonic rat trabecular meshwork cells, transfected with plasmid DNA containing the EcMscL-mCherry gene, in ~2 U/mL Alexa Fluor™ 488 Phalloidin dye. 15 minutes after a hypo-osmotic shock (addition of 20% v/v water). 488 nm excitation and 505-525 nm emission filter. FIG. 4J. Kinetics of the intensity of green fluorescence in cells, showing only EcMscL expressing cells uptake the dye, while non transfected cells stay dark.

FIG. 5A. Principle of the response of cells sensitized with MscL to membrane tension/deformation induced by mechanical force stimuli.

The MGP-EcMscL-mCherry gene packaged in AAV8 virus and delivered to anterior chamber of mice eyes via intracameral injection led to expression in trabecular meshwork (TM). FIG. 6A. Confocal DAPI stained (blue fluorescence) image of Irido-corneal region of a cross-section of an eye treated with MGP-EcMscL-mCherry gene packaged in AAV8 virus showing the cells in cornea and TM. FIG. 6B. Confocal anti-mCherry antibody stained (red fluorescence) of the cross-section of the eye treated with MGP-EcMscL-mCherry gene packaged in AAV8 virus. The strong red fluorescence of reporter (mCherry) seen in the TM shows successful targeted expression of EcMscL-mCherry in the TM. FIG. 6C. Elevated IOP in mice treated with topical application of 0.1% dexamethasone (DEX) 3 times daily. (N=7). FIG. 6D. Decrease in intraocular pressure (IOP) of OD eye 3 weeks after intracameral injection of virally carried EcMscL into OD eye targeted to the TM. (N=4). Average±Std. Dev. FIG. 6E. IOP decrease in contralateral (OS) eye 3 weeks after intracameral injection of virally carried EcMscL in the OD eye. (N=4). Average±Std. Dev.

FIG. 7. Confocal Image of the flat-mount mouse retina transfected with EcMscL-double mutant (I113L/I70E, SEQ ID No. 5) via intravitreal injection and nano-enhanced optical delivery (NOD), a type of non-viral (laser assisted) gene delivery. As laser irradiation was done in the rectangular region (marked by dotted boundary), the anti-mCherry antibody immune-stained retina shows red fluorescence in transfected area.

The MGP-EcMscL (SEQ ID NO. 1)-mCherry gene packaged in AAV8 virus and delivered via lateral tail vein injection to a mice led to expression in brain regions. FIG. 8A. DAPI stained confocal (blue fluorescence) image of the brain section of a mouse transfected with EcMscL-mCherry in the cerebellum region. The scale bar is 20 micron. FIG. 8B. Confocal anti-mCherry antibody stained (red fluorescence) image showing transfection and EcMscL expression at the edge of cerebellum. The arrows show transfected regions. FIG. 8C. DAPI stained confocal (blue fluorescence) image of the brain section of a mouse transfected with EcMscL-mCherry in the Pons and Medulla region. FIG. 8D. Confocal anti-mCherry antibody stained (red fluorescence) image showing transfection and EcMscL expression in the Pons and Medulla region. The arrows show transfected regions.

Figure 9A:
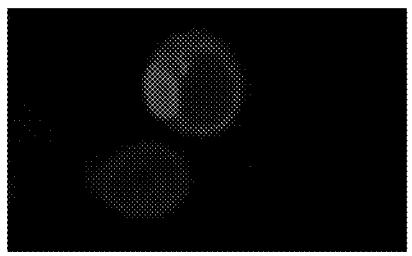
Figure 9B:
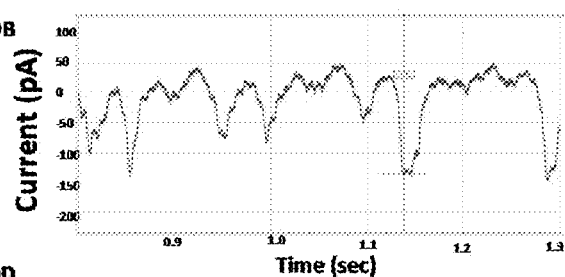
Figure 9C:
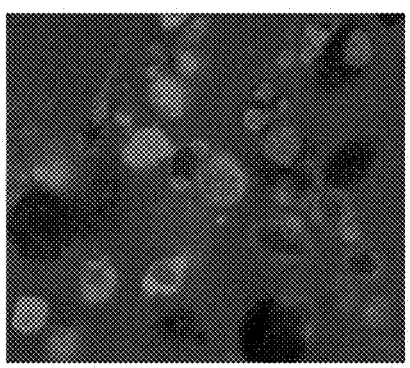
Figure 9D:
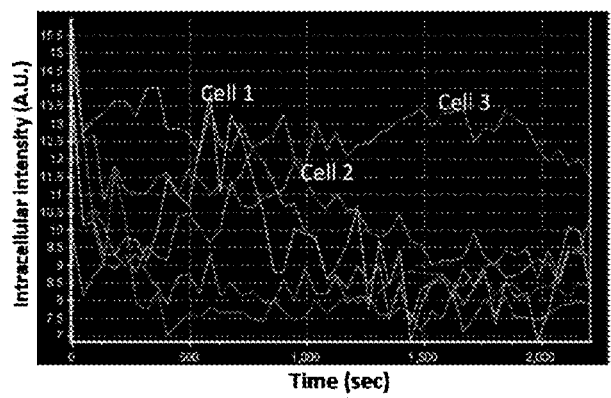

FIG. 9A. Confocal image of reporter (mCherry) fluorescence transfected HEK293 cells expressing MtMscL-mCherry (see SEQ ID NO. 2) showing plasma membrane localization of the protein expression. FIG. 9B. Inward current profile of a patched MtMscL expressing HEK293 cell after hypotonic shock (addition of 20% v/v water). FIG. 9C. Overlay of red and green filtered confocal images of HEK293 cells transfected with the MtMscL-mCherry gene in solution containing the membrane impermeable dye (Alexa Fluor™ 488 carboxylic acid succinimidyl ester, green) 25 minutes after hypotonic shock. The image shows uptake of the dye (green fluorescence) only in MtMscL expressing cells. FIG. 9D. Kinetics of the intensity of green fluorescence in cells showing MtMscL expressing cells (e.g., Cell 1, Cell 2, Cell 3) uptake the dye, while non-transfected cells stay dark.

Figure 10A:
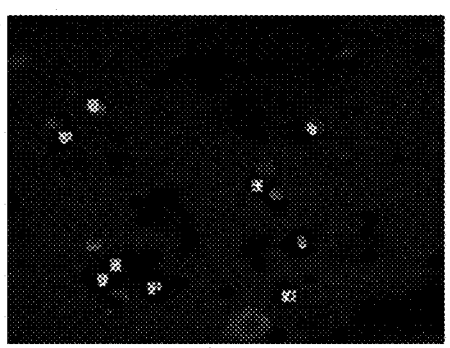
Figure 10B:
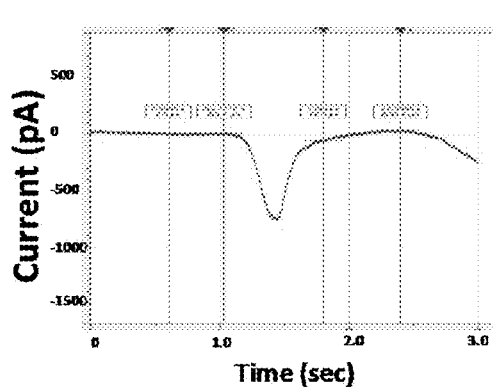
Figure 10C:
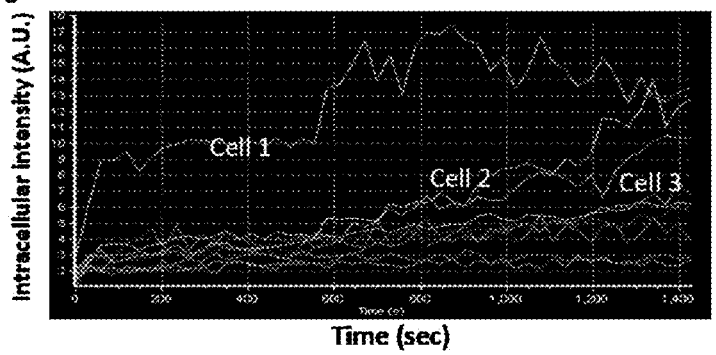

FIG. 10A. Confocal image of HEK293 cells transfected with the EcMscL (I113L/I70E)-mCherry gene (see SEQ ID NO. 5) in solution containing the membrane impermeable dye, Alexa Fluor™ 488 carboxylic acid succinimidyl ester. FIG. 10B. Inward current profile of a patched EcMscL (I113L/I70E) expressing HEK293 cell in response to a hypotonic shock (addition of 20% v/v water). FIG. 10C. Kinetics of the intensity of green fluorescence of the membrane impermeable dye (Alexa Fluor™ 488 carboxylic acid succinimidyl ester) in cells, showing only EcMscL (I113L/I70E) expressing cells (e.g., Cell 1, Cell 2, Cell 3) uptake the dye, while non-transfected cells stay dark.

Figure 11A:
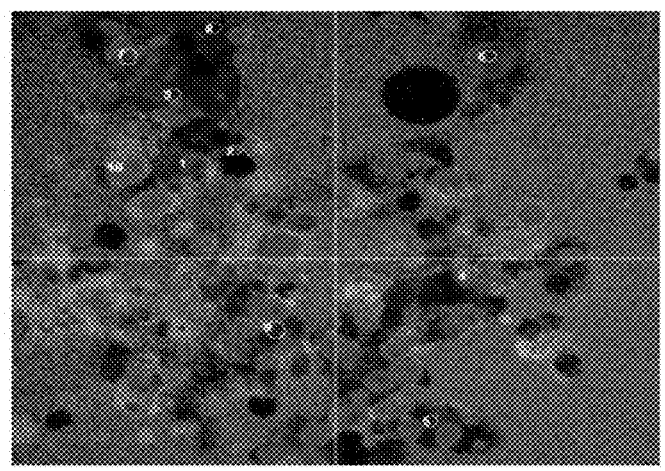
Figure 11B:
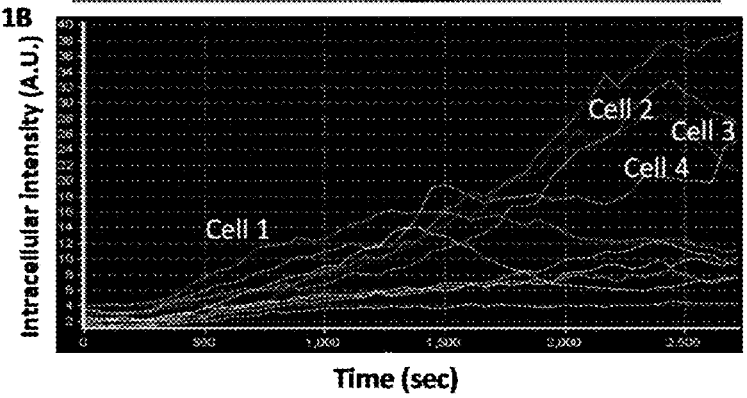

FIG. 11A. Overlay of red and green filtered confocal images of HEK293 cells transfected with the VcMscL-mCherry gene (see SEQ ID NO. 4) in solution containing the membrane impermeable dye, Alexa Fluor™ 488 carboxylic acid succinimidyl ester. FIG. 11B. Kinetics of the intensity of green fluorescence in cells, showing only VcMscL expressing cells (e.g., Cell 1, Cell 2, Cell 3 and Cell 4) uptake the membrane impermeable dye, Alexa Fluor™ 488 carboxylic acid succinimidyl ester, while non-transfected cells stay dark.

Figure 12A:
Figure 12B:
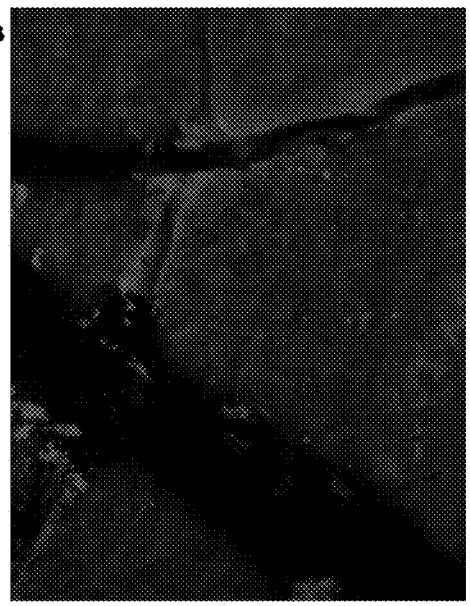

FIG. 12A. Confocal Image of anti-mCherry antibody immune-stained blood vessels in mouse. FIG. 12B. Confocal Image of anti-mCherry antibody immune-stained blood vessels in mouse transfected with EcMscL-double mutant (I113L/I70E, SEQ ID No. 5) showing red fluorescence in the walls of blood vessels.

FIG. 13. Extracellular potential of EcMscL expressing HEK293 cells grown on a multi-electrode array (MEA) petri dish in response to hypotonic shock (addition of 20% v/v water). Burst of spikes can be seen in the signal during 13-14.5 sec, demonstrating robust EcMscL channel activities.

FIG. 14A. Extracellular potential of HEK293 cells (−ve control) grown on a multi-electrode array (MEA) petri dish. FIG. 14B. Ultrasound stimulation (Pulse width: 250 ms, Repetition rate: 2 Hz, Frequency: 1.1 MHz) induced EcMscL channel activities in EcMscL expressing HEK293 cells measured by extracellular potential using a multi-electrode array (MEA) petri dish.

Figure 15:
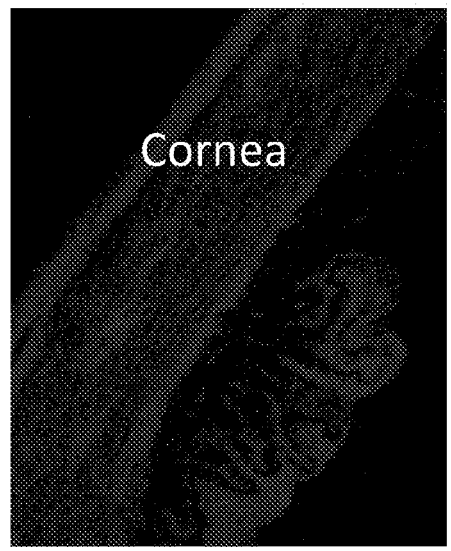

FIG. 15. Confocal Image of the mouse cornea transfected with EcMscL-mCherry via AAV8 based gene transduction. Expression of reporter-mCherry exhibited by red fluorescence.

Figure 16A:
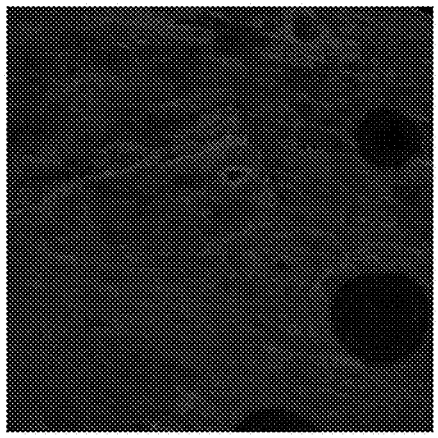
Figure 16B:
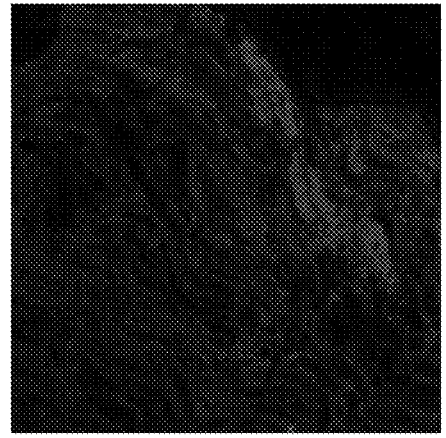
Figure 16C:
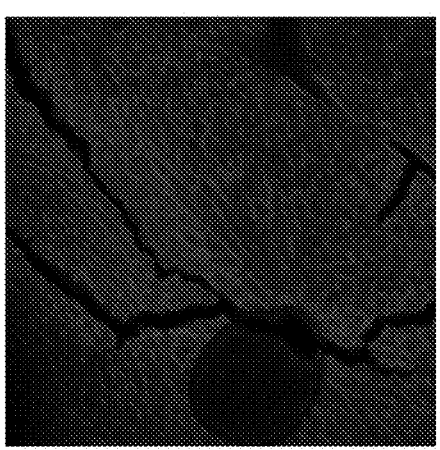
Figure 16D:
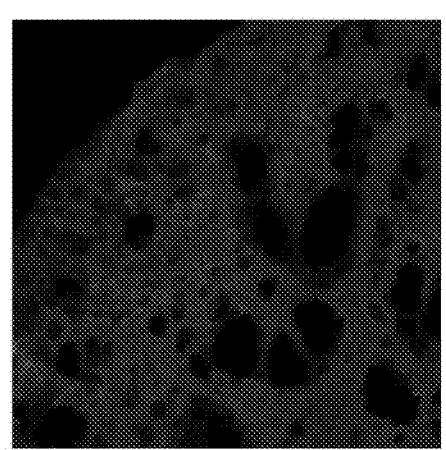

FIG. 16A. Confocal Image of the mouse Heart transfected with EcMscL-mCherry via AAV based gene transduction. Expression of reporter-mCherry exhibited by red fluorescence. FIG. 16B. Confocal Image of the mouse Kidney transfected with EcMscL-mCherry via AAV based gene transduction. Expression of reporter-mCherry exhibited by red fluorescence. FIG. 16C. Confocal Image of the mouse Liver transfected with EcMscL-mCherry via AAV based gene transduction. Expression of reporter-mCherry exhibited by red fluorescence. FIG. 16D. Confocal Image of the mouse Lung transfected with EcMscL-mCherry via AAV based gene transduction. Expression of reporter-mCherry exhibited by red fluorescence.

DETAILED DESCRIPTION OF THE INVENTION

Glaucoma has been nicknamed "the sneak thief of sight", because its onset often has no symptoms and sufferers belatedly become aware of a problem only when their vision is significantly diminished. Although glaucoma is more prevalent in the elderly, African-Americans, diabetics and those who have family members with the disease, people of all demographics are still susceptible to developing it. Glaucoma is recalcitrant to treatment and the resulting optic nerve damage is irreversible. The development of a safe effective single-dose long-lasting treatment for glaucoma would improve the lives of many glaucoma patients and revolutionize the way we treat glaucoma.

Glaucoma is defined as a group of eye conditions which cause damage to the optic nerve, usually due to elevated IOP (Intra Ocular Pressure). A healthy intraocular pressure (IOP) is maintained by continuous upkeep of vitreous and aqueous humor processing. In the case of Glaucoma patients there is a restriction in the flow of aqueous humor through the trabecular meshwork, which blocks drainage into Schlemm's canal and episcleral blood vessels, leading to elevated IOP. There are four main avenues by which IOP can be decreased; i) reduce aqueous humor production, ii) increase outflow through the uveoscleral pathway, iii) improve drainage through the conventional pathway, or iv) create an alternate outflow pathway.

Current pharmaceutical and surgical glaucoma treatments have significant limitations and side effects. The traditional pharmaceutical approach involves the delivery of a drug by daily doses of eyedrops, ointments, or oral tablets. Besides undesirable side effects, the major problem with these patient-dependent treatment protocols is poor patient compliance. To address compliance issues, researchers have begun developing non-invasive ocular implants that slowly release a drug into the eye over the period of a few months. However, many patients will still need constant adjustments to their medications and dosing regimens over time due to changes in their drug responsiveness and disease condition.

Surgical method options include, trabeculectomy, canaloplasty, laser trabeculoplasty, laser peripheral iridotomy, deep non-perforating sclerectomy, and drainage device implantation. As with all surgeries, there are risks of infection, systemic side effects and human/device failure. Post-surgical scarring at the procedure site is common and scar tissue can block or shift the newly created drainage pathway. With the added considerations of the expense, patient recovery time and inconsistent outcomes of surgery, it becomes clear that new and innovative treatments for glaucoma are needed.

As an alternative to surgical and pharmacological treatments, this invention describes a novel and unique method and compositions to treat glaucoma. The present invention provides a method to lower IOP, thereby preventing continued optic nerve damage in glaucoma patients.

It has been estimated that 80-90% of aqueous humor drainage is through the conventional outflow pathway. Studies have also elucidated that in many cases of POAG. increased IOP is associated with increased outflow resistance through the TM. Therefore it is striking to discover that few existing glaucoma surgical procedure and only one recently FDA-approved glaucoma drug, address the improvement of outflow through the conventional outflow pathway[3,4]. Instead they either reduce aqueous humor production (e.g. Beta-blockers) or increase uveoscleral outflow (e.g. prostaglandin analogs).

In an embodiment, this invention provides a method and composition that wherein it exploits an exogenous macromolecular pressure sensor and outflow actuator to regulate IOP by increasing outflow facility through the TM.

In another embodiment, this invention provides a method and composition, wherein exogenous macromolecular pressure sensor is the mechanosensitive channel of large conductance and its variants.

In yet another embodiment, MscL proteins of SEQ ID 1-4 and its site generated mutants when expressed on mammalian cell membrane, senses pressure changes and modulate the intra cellular pressure or molecular transport not limited to aqueous fluid and therapeutic molecules.

In another embodiment of the invention, the present invention describes a method and compositions, wherein the MscL homologues strains include but not limited to bacterial, fungi, yeast etc.

In yet another embodiment, the present invention describes the compositions, wherein the MscL homologues strains includes but not limited to MscLs from *Escherichia coli, Mycobacterium Tuberculosis, Vibrio cholera, Bacillus subtilis, Mycobacterium leprae, Chlorobium tepidum, Thermus thermophilus, Haemophilus influenza, Erwinia carotovora, Pseudomonas fluorescens, Clostridium perfringens, Staphylococcus aureus, Streptococcus faecalis, Lactococcus lactis, Brucella melitensis, Caulobacter crescentus, Clostridium histolyticum, Fusobacterium nucleatum* subsp, *Mesorhizobium loti, Pasteurella multocida, Pectobacterium carotovorum, Pseudomonas aeruginosa, Salmonella enterica serovar Typhimurium, Salmonella enterica serovar Typhi, Xylella fastidiosa, Corynebacterium glutamicum, Deinococcus radiodurans, Lactococcus lactis, Ralstonia solanacearum, Sinorhizobium meliloti, Streptococcus pneumoniae, Streptococcus pyogenes, Streptomyces coelicolor, Methanosarcina acetivorans Listeria innocua, Listeria monocytogenes* etc.

In yet another embodiment, The present disclosure also provides for the modification of MscL proteins expressed in a cell by the addition/Deletion, truncation or substitution of one or more amino acid sequence motifs which enhance transport to the plasma membranes of mammalian cells. Consequently, in Some embodiments, MscL protein expressed in a cell is fused to one or more amino acid sequence motifs selected from the group consisting of a signal peptide, an endoplasmic reticulum (ER) export signal, a membrane trafficking signal, and an N-terminal Golgi export signal. The one or more amino acid sequence motifs which enhance MscL protein transport to the plasma membranes of mammalian cells can be fused to the N-terminus, the C-terminus, or to both the N- and C-terminal ends of the MscL protein.

Another aspect of this invention describes the viral delivery of a transgene encoding for the mechanosensitive channel of large conductance (MscL) to TM cells where, once translated and incorporated into the cell membrane, the channel can facilitate the movement of fluid out of the cell in response to an increase in IOP.

In an embodiment, the present invention provides a method and composition wherein a portion of the excreted cellular fluid will drain into Schlemm's canal and on into the vascular system, thereby reducing the volume of fluid in the eye. Logically, this decrease in fluid volume will result in a decrease in IOP.

Previous studies have shown that, when the contractility of TM cells is inhibited, the cells change shape, thereby creating more intercellular space and consequently improving AH outflow facility through the TM. Another aspect of this invention is that the activation of MscL will have a similar benefit, because the resulting decrease in cell size should also create more intercellular space and increase paracellular aqueous humor transport.

In another embodiment, the present invention provides a method and composition wherein cellular recovery processes caused by the shift in cellular equilibrium after MscL activation, may trigger several signaling cascades that could affect TM cell function. For example, in bacteria it has been shown that expression of heat shock proteins is upregulated after MscL gating during hypo-osmotic shock. In Parallel, it has been shown that glaucomatous TM cells expressing mutant myocilin (a cause of POAG in some patients) have increased outflow resistance, but when protein-folding chaperones (including heat shock proteins) are co-expressed, outflow facility improves. It is believed this improvement is due to the chaperones preventing mutant myocilin-induced protein aggregation, which restores function to the cells. With these two studies in mind, one can postulate that if MscL activation triggers heat-shock protein expression in mutant myocilin-induced glaucoma TM cells, then AH outflow facility should also be improved.

In yet another embodiment, the present invention provides a method and composition wherein the activation of MscL leads to fluid expulsion into Schlemm's canal, cell shrinkage and increased intercellular spaces and triggers cellular processes that may upregulate protective genes.

Another aspect of the invention describes MscL as an autonomous sensor and actuator that does not need partners or energy sources to function. MscL intrinsically senses tension in the membrane lipid bilayer and gates in direct response to this mechanical stimulation.

In a preferred embodiment, the present invention describes a method and composition wherein an Adeno-associated virus (AAV) compatible plasmid DNA construct, encoding the MscL gene and a TM-specific promoter, leads to the expression of MscL in TM cells. Preferably, *Escherichia coli* MscL (EcMscL), is selected because it is the most robust and well characterized MscL homolog. The MscL gene from the BL21(DE3) *Escherichia coli* strain, which encodes for a136 amino acid monomer, was retrieved and codon optimized for mammalian cell expression. The gene was put under the control of a TM-specific promoter. Several studies have shown that in the eye matrix Gla protein (MGP) is preferentially expressed in TM cells and its promoter sequence has been used to target gene expression. The MGP promoter sequence (pMGP) located on chromosome 12, 14886367-14885792 was identified by using the primers from Linton et al. (2005) to run an alignment search against the reverse compliment strand of human genome GRCh38.p12. The resulting 576 bp promoter sequence was placed on the 5' end of the EcMscL gene. A fused fluorescent reporter was chosen to act as a visual marker of gene expression and membrane localization. As EcMscL is a homo-oligomer and needs to assemble into a functional complex postranslationally, a strictly monomeric fluorescent protein had to be chosen to avoid any disruptive interactions. To this end the monomeric fluorescent protein, m-Cherry, was C-terminally fused to MscL. Finally, the pAAV-MCS plasmid backbone is a salient base, because it has been reportedly used successfully in viral delivery of genes to the HTM.

In another embodiment, this invention describes a method wherein primary cultured TM cells are transfected with MscL plasmid DNA by lipofection and protein expression and localization were assayed by epifluorescence confocal microscopy. Cells were also monitored by transmission microscopy to check for any changes to their morphology or growth cycle. Protein localization studies using anti-mCherry(reporter) antibodies was performed using western blot.

In yet another embodiment, this invention provides a method, wherein retention of EcMscL native function in the TM cell membrane is shown through electrophysiological measurements of channel gating recordings from membrane patches excised from the surface of EcMscL expressing HTM cells. Mechanical stimulation was induced by applying suction to the patch clamp pipette to create negative pressure.

In another embodiment, the present invention provides a method and composition wherein mechanosensitive channels can be expressed in other cells of the eye for the treatment of glaucoma. The ocular cells include, but are not limited to, Schlemm's canal, retinal ganglion, glial, cilliary body, corneal, bipolar and photoreceptor cells. In this role, mechanosensitive channels can act as osmoregulators, influence the production and composition of aqueous and vitreous humor, protect compression stress, supplement neural activity, and such other functions.

In another aspect of this present invention, wherein the methods and compositions of mechanosensitive channels refers to all known mechanically/stretch activated channels and proteins, which include, but are not limited to, MscS, MscK, MscG, MSL2-MSL10, MCA, TPK, piezo channels, TRVP1-TRPV5, OSM-9, Mys1, Mys2 and MSC1.

Another aspect of the present invention describes a method wherein heterologously expressed mechanosensitive channels, such as bacterial mechanosensitive channels (MscL, MscS, MscK, MscG), plant mechanosensitive channels (MSL2-10), TRPV1-TRPV5 channels, Piezo channels or their generated site-directed mutants are used as osmoregulators, activated by internal or external mechanical stimuli, in the epithelial cells of the arterial system in the treatment and prevention of hypo- as well as hyper-tension.

In another embodiment of the invention, the present invention describes a method wherein the mechanosensitive channels, such as bacterial mechanosensitive channels (MscL, MscS, MscK, MscG), plant mechanosensitive channels (MSL2-10), TRPV1-TRPV5 channels, Piezo channels or their generated site-directed mutants, when expressed in the Hematopoietic stem cells, will generate red blood cells which act as osmoregulators and resistant to osmotic shock, in the treatment and prevention of hyper- as well as hypotension related diseases.

In another embodiment of the invention, the present invention describes a method wherein heterologously expressed mechanosensitive channels, such as bacterial mechanosensitive channels (MscL, MscS, MscK, MscG), plant mechanosensitive channels (MSL2-10), TRPV1-TRPV5 channels, Piezo channels or their generated site-directed mutants are used as osmoregulators or diuretics, activated by internal or external mechanical stimuli, in the renal system in the treatment and prevention of kidney stones and chronic kidney disease.

Another aspect of the present invention describes a method wherein heterologously expressed mechanosensitive channels, such as bacterial mechanosensitive channels (MscL, MscS, MscK, MscG), plant mechanosensitive channels (MSL2-10), TRPV1-TRPV5 channels, Piezo channels or their generated site-directed mutants are used as bile regulators, activated by internal or external mechanical stimuli, in liver, gallbladder or bile duct cells of the hepatic system in the treatment and prevention of gallstones.

Another aspect of the present invention describes a method, wherein heterologously expressed mechanosensitive channels, such as bacterial mechanosensitive channels (MscL, MscS, MscK, MscG), plant mechanosensitive channels (MSL2-10), TRPV1-TRPV5 channels, Piezo channels or their generated site-directed mutants, are used as osmoregulators, activated by internal or external mechanical stimuli, and alternative outflow/inflow pathway for fluid in the treatment and prevention of edemas. These diseases include, but are not limited to, passive subretinal, cystoid macular, lymph-, peripheral, pulmonary, and pedal edemas as well as osteoarthritis related swollen knees and joints.

In another embodiment of the invention, the present invention describes a method wherein heterologously expressed mechanosensitive channels, such as bacterial mechanosensitive channels (MscL, MscS, MscK, MscG), plant mechanosensitive channels (MSL2-10), TRPV1-TRPV5 channels, Piezo channels or their generated site-directed mutants, in reproductive system are used as osmoregulators, and alternative outflow/inflow pathway for fluid, activated by internal or external mechanical stimuli, in the treatment and prevention of erectile dysfunction, vaginal dryness, benign prostatic hyperplasia and polycystic ovary syndrome.

In yet another embodiment of the invention, the present invention describes a method wherein heterologously expressed mechanosensitive channels, such as bacterial mechanosensitive channels (MscL, MscS, MscK, MscG), plant mechanosensitive channels (MSL2-10), TRPV1-TRPV5 channels, Piezo channels or their generated site-directed mutants, are used as osmoregulators, activated by internal or external mechanical stimuli, and alternative outflow/inflow pathway for fluid in the treatment of any skin related diseases such as dysfunction of sweat glands etc.

In yet another embodiment of the invention, the present invention describes a method wherein heterologously expressed mechanosensitive channels, such as bacterial mechanosensitive channels (MscL, MscS, MscK, MscG), plant mechanosensitive channels (MSL2-10), TRPV1-TRPV5 channels, Piezo channels or their generated site-directed mutants, are used as macromolecular pressure release valves, activated by internal or external mechanical stimuli, and alternative outflow pathway for fluid in the treatment of idiopathic intracranial hypertension.

In another embodiment of the invention, the present invention describes a method of wherein heterologously expressed mechanosensitive channels, such as bacterial mechanosensitive channels (MscL, MscS, MscK, MscG), plant mechanosensitive channels (MSL2-10), TRPV1-TRPV5 channels, Piezo channels or their generated site-directed mutants are used as transmembrane ports in cells activated by internal or external mechanical stimuli for enhanced drug delivery in order to increase efficacy of the treatment for diseases including cancer.

Another aspect of the present invention describes a method wherein the expression of said mechanosensitive channel in cancer cells, targeted by specific receptors such as EGFR, or pH environment, is used to precipitate cell death by either bioengineering a constitutively open "leaky" channel or through overstimulation of the channel.

Another aspect of the present invention describes a method wherein heterologously expressed mechanosensitive channels, such as bacterial mechanosensitive channels (MscL, MscS, MscK, MscG), plant mechanosensitive channels (MSL2-10), TRPV1-TRPV5 channels, Piezo channels or their generated site-directed mutants, are used for stimulation of cells, including neurons, cardiac and muscle cells for treatment and prevention diseases including but not limited to, neurological diseases such as pain, epilepsy, stroke as well as cardiovascular diseases and muscular dystrophies.

In another embodiment of the invention, the present invention describes a method of wherein heterologously expressed mechanosensitive channels, such as bacterial mechanosensitive channels (MscL, MscS, MscK, MscG), plant mechanosensitive channels (MSL2-10), TRPV1-TRPV5 channels, Piezo channels or their generated site-directed mutants, in neurons are activated by internal or external mechanical stimuli, for modulating neural activities in order to repair injury such as concussion, enhance neural regeneration, accelerated learning and memory processing.

In another embodiment of the invention, the present invention describes a method wherein heterologously expressed mechanosensitive channels, such as bacterial mechanosensitive channels (MscL, MscS, MscK, MscG), plant mechanosensitive channels (MSL2-10), TRPV1-TRPV5 channels, Piezo channels or their generated site-directed mutants, in neurons are activated by internal or external mechanical stimuli, for modulating activities in dormant neurons in order to recover from coma, and persistent vegetative state.

In yet another embodiment of the invention, the present invention describes a method wherein heterologously expressed mechanosensitive channels, such as bacterial mechanosensitive channels (MscL, MscS, MscK, MscG), plant mechanosensitive channels (MSL2-10), TRPV1-TRPV5 channels, Piezo channels or their generated site-directed mutants are used as osmoregulators, activated by internal or external mechanical stimuli, in the central nervous system (CNS) mediated barriers such as blood-cerebrospinal fluid (CSF) barrier, the blood brain barrier (BBB), the blood-retinal barrier and the blood-spinal cord barrier etc.

Another aspect of the present invention describes a method wherein heterologously expressed mechanosensitive channels, such as bacterial mechanosensitive channels (MscL, MscS, MscK, MscG), plant mechanosensitive channels (MSL2-10), TRPV1-TRPV5 channels, Piezo channels or their generated site-directed mutants, activated by internal or external mechanical stimuli, are used as efflux ports for allowing the clearance of toxins such as Beta-Amyloid, Tau, Alpha-synuclein and PolyQ from central nervous system to the blood stream via the blood brain barrier (BBB), the blood-retinal barrier and the blood-spinal cord barrier in neurodegenerative diseases including but not limited to Alzheimer's, Parkinson's, and Huntington's disease.

Another aspect of the present invention describes a method wherein mechanosensitive channels, such as bacterial mechanosensitive channels (MscL, MscS, MscK, MscG), plant mechanosensitive channels (MSL2-10), TRPV1-TRPV5 channels, Piezo channels or their generated site-directed mutants, heterologously expressed in Pneumocytes, activated by internal or external mechanical stimuli, are used as ports for exchange of oxygen and Carbon dioxide from alveolus to the blood capillaries and vice a versa via the Pneumocytes in lung diseases including but not limited to Black Lung Disease (Coal workers' pneumoconiosis).

In yet another embodiment of the invention, the present invention describes a method wherein the cells expressing the mechanosensitive channels such as bacterial mechanosensitive channels (MscL, MscS, MscK, MscG), plant mechanosensitive channels (MSL2-10), TRPV1-TRPV5 channels, Piezo channels or their generated site-directed mutants, with or without fusion or conjugation of nanoprobes, are activated by a device providing external mechanical force or magnetic field, whose duration, frequency and strength can be tuned for controlled stimulation, molecular delivery or cellular death leading to the desired therapeutic outcome.

The present disclosure will now be described more fully hereinafter with reference to the accompanying drawings, in which some exemplary embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

The use of the word "a" or "an" when used in conjunction with the term "comprising" in the claims and/or the specification may mean "one," but it is also consistent with the meaning of "one or more," "at least one," and "one or more than one."

The use of the term "or" in the claims is used to mean "and/or" unless explicitly indicated to refer to alternatives only or the alternative are mutually exclusive, although the disclosure supports a definition that refers to only alternatives and "and/or."

The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the terms "substantially," "approximately," and "about" may be substituted with "within [a percentage] of" what is specified, where the percentage includes 0.1, 1, 5, and 10 percent.

Throughout this application, the term "about" is used to indicate that a value includes the standard deviation of error for the device or method being employed to determine the value.

Further, a molecule or method that is configured in a certain way is configured in at least that way, but it can also be configured in other ways than those specifically described.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, an apparatus that "comprises," "has," "includes" or "contains" one or more elements possesses those one or more elements, but is not limited to possessing only those elements. Likewise, a method that "comprises," "has," "includes" or "contains" one or more steps possesses those one or more steps, but is not limited to possessing only those one or more steps.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Any embodiment of any of the apparatuses, systems, and methods can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

To the extent that any specific disclosure in the aforementioned references or other literature may be considered to anticipate any generic aspect of the present invention, the disclosure of the present invention should be understood to include a proviso or provisos that exclude of disclaim any such species that were previously disclosed. The aspects of the present invention, which are not anticipated by the disclosure of such literature, are also nonobvious from the disclosure of these publications, due at least in part to the unexpectedly superior results disclosed or alleged herein.

Below, the presently disclosed invention will be further described by way of examples, which are provided for illustrative purposes only and accordingly are not to be construed as limiting the scope of the invention.

EXAMPLES

Example 1

The experiments outlined below demonstrate that bacterial mechanosensitive channels can be expressed in mammalian cells, especially trabecular meshwork cells. *Escherichia coli* MscL (EcMscL), has been selected as a model channel because it is the most robust and well characterized mechanosensitive channel. The MscL gene from the BL21 (DE3) *E. coli* strain, which encodes for a 136 amino acid monomer, was codon optimized for mammalian cell expression and was put under the control of a TM-specific promoter. Several studies have shown that in the eye matrix Gla protein (MGP) is preferentially expressed in TM cells and its promoter sequence has been used to target gene expression. The MGP promoter sequence (pMGP) located on chromosome 12, 14886367-14885792 was identified by using the primers from Linton et al. (2005) to run an alignment search against the reverse compliment strand of human genome GRCh38.p12. The resulting 576 bp promoter sequence was placed on the 5' end of the EcMscL gene. A fused fluorescent reporter was chosen to act as a visual marker of gene expression and membrane localization. As EcMscL is a homo-oligomer and needs to assemble into a functional complex post-translationally, a strictly monomeric fluorescent protein had to be chosen to avoid any disruptive interactions. To this end the monomeric fluorescent protein, m-Cherry, was C-terminally fused to MscL. This designed DNA segments were inserted into a vector between two restriction sites, BamHI and SalI [FIG. 1A and FIG. 1B]. Two mammalian cell types were transfected with the pMGP-EcMscL-mCherry construct: HEK239 cells and primary embryonic rat trabecular meshwork cells. Both cell types were cultured in 1 mL of standard DMEM growth media in 35 mm petri dishes. JetPRIME (PolyPlus) was used to deliver 2 μg of pMGP-EcMscL-mCherry plasmid DNA to each dish. Fluorescent confocal microscopy of live cells was used to confirm the successful transfection and expression of the fluorescent reporter linked gene. The samples were excited at 488 nm and a 560-660 nm red emission filter was used to visualize mCherry fluorescence. A population of HEK293 cells [FIG. 2A and FIG. 2B] and embryonic rat trabecular meshwork cells [FIG. 3A and FIG. 3B] were fluorescent, thereby indicating that MscL can be expressed in mammalian hosts that are biosimilar to the intended host (human cells).

Example 2

The experiment outlined below demonstrates that bacterial mechanosensitive channels retain their native function in mammalian cells and can be used for molecular delivery and osmotic pressure control. EcMscL is an osmoregulator and gates in response to stretching of the cell membrane caused by turgor pressure. When the EcMscL channel opens, membrane impermeable molecules are able to diffuse into and out of the cell through the open pore. Therefore, when subjected to a hypo-osmotic shock in the presence of extracellular membrane impermeable molecules (including dyes or therapeutic agents), cells expressing functional EcMscL should uptake the molecule(s). Primary cultured embryonic rat trabecular meshwork cells transfected with pMGP-EcMscL-mCherry plasmid DNA were subjected to a hypo-osmotic shock in the presence of 2 U/mL Alexa Fluor™ 488 carboxylic acid succinimidyl ester (Invitrogen) by the addition of 20% water v/v. The cells were then monitored by confocal fluorescence microscopy for 15 minutes at 488 nm excitation and detected though either a green emission filter (505-525 nm). Bright field and fluorescence images show that after hypo-osmotic shock, only red (emission filter: 560-660 nm) fluorescent EcMscL expressing cells uptake the green dye [FIG. 4A to FIG. 4I]. Analysis of fluorescence images show that after hypo-osmotic shock, only red fluorescent EcMscL expressing cells uptake the green dye [FIG. 4J]. Non-fluorescent cells stay swollen and dark after the osmotic down shock indicating there was no EcMscL activity (i.e. no transport of extra-cellular impermeable dye Alexa Fluor™ 488 carboxylic acid succinimidyl ester). Therefore, we can deduce that red fluorescence is correlated with EcMscL activity and that transfection of the EcMscL-mCherry construct led to the expression of a functional membrane-integrated EcMscL-mCherry channel protein that led to osmoregulation and molecular delivery.

Example 3

FIG. 5A shows the principle of the response of cells sensitized with MscL to membrane tension/deformation induced by mechanical force stimuli. The experiment outlined below demonstrates that bacterial mechanosensitive channels retain their native functional in mammalian cells and can be stimulated by external mechanical or osmotic pressure. EcMscL channel function in mammalian cells was probed by recording electrophysiological measurements from whole cell patches of HEK293 and embryonic rat TM cells expressing EcMscL-mCherry. The patch-clamp recording setup includes an inverted Nikon fluorescence microscope (TS 100) platform using an amplifier system (Axon Multiclamp 700B, Molecular Devices). Micropipettes were pulled using a two-stage pipette puller (Narshinghe) to attain resistance of 3 to 5 MΩ when filled with a solution containing (in mM) 130 K-Gluoconate, 7 KCl, 2 NaCl, 1 $MgCl_2$, 0.4 EGTA, 10 HEPES, 2 ATP-Mg, 0.3 GTP-Tris and 20 sucrose. The micropipette-electrode was mounted on a micromanipulator. The extracellular solution contained (in mM): 150 NaCl, 10 Glucose, 5 KCl, 2 $CaCl_2$, 1 $MgCl_2$ was buffered with 10 mM HEPES (pH 7.3). Photocurrents were measured while holding cells in voltage clamp at −70 mV. The electophysiological signals from the amplifier were digitized using Digidata 1440 (Molecular devices), interfaced with patch-clamp software (Clampex, Molecular Devices). pClamp 10 software was used for data analysis. Channel activity was induced by subjecting the patched cell to a hypo-osmotic shock by the addition of 20% v/v water [FIG. 2C and FIG. 3C]. A stable GigaOhm seal was achieved and the current traces show channel activity in response to the hypo-osmotic shock. A comparison of channel activity in HEK293 cells and embryonic rat TM cells show a difference in peak current and open dwell times [FIG. 3D].

Example 4

The experiments outlined below demonstrate that when expressed in the trabecular meshwork (TM), EcMscL can lower intraocular pressure (IOP) and thereby treat glaucoma. Studies on the effect of virally delivered EcMscL on IOP were carried out in a glucocorticoid-induced mouse model of glaucoma. To induce elevated IOP in wild-type C57BL/6J mice, 0.1% dexamethasone (DEX) ophthalmic solution was administered to the mouse eye three times daily for the duration of the study. IOP was measured using a TonoVet (a rebound tonometer). The IOP readings for each eye were taken 3 times and the mean measurement was recorded. The control group mice [FIG. 6C] showed elevated IOP. Another group of mice was treated with intracameral injection of adeno-associated virus (AAV) containing the EcMscL-mCherry gene into the anterior chamber of the eye (AAV2/8-pMGP-EcMscL-mCherry ($6.75 \times 10^{10}$ gc/eye)). The needle was inserted through the cornea, anterior to the iridocorneal angle, and 3 μl of virus was pumped into the eye at a rate of 1 μl/min. The needle was left in place in the eye for 1 min after injection and then slowly retracted. IOP was taken before treatment and weekly after that. The IOP was found to decrease [FIG. 6D, FIG. 6E] 3 weeks after intracameral injection of virally carried EcMscL targeted to the TM as compared to untreated control mice group [see FIG. 6C]. At the end of the study, mice were sacrificed and their eyes sectioned for immunohistochemical analysis. Immunostaining with anti-mCherry antibody showed that EcMscL-mCherry was successfully expressed in the TM [see FIG. 6A, FIG. 6B]. The results of this study show that the expression of EcMscL in the TM can be correlated with reduction in elevated IOP and demonstrate the utility of mechanosensitive channels in the treatment of glaucoma. Thus, the heterologously expressed mechanosensitive channels, such as bacterial mechanosensitive channels (MscL) or their generated site-directed mutants, used as osmoregulators, are activated by internal or external mechanical stimuli, and alternative outflow/inflow pathway for fluid in the treatment and prevention of edemas such as passive sub-retinal, cystoid macular, lymph-, peripheral, pulmonary, and pedal edemas as well as osteoarthritis related swollen knees and joints.

Example 5

The experiment outlined below demonstrates that EcMscL (I113L/I70E)-mCherry (See SEQ ID NO. 5) can be delivered to the spatially-targeted tissue area of an organ in-vivo by non-viral methods. The laser assisted gene delivery method used is called nano-enhanced optical delivery (NOD) wherein low power continuous wave laser beam is enhanced locally due to surface plasmon resonance near the tissue by the gold nanoparticles to create transient perforation of cell membrane by localized temperature rise at hotspots. Though any tissue can be targeted, retina was used as an example. First, the mouse eye was injected intravitreally with 1 µl of gold nanorods (GNRs). After ~30-45 min, the eye was injected intravitreally again with 1 µl of plasmid DNA containing the EcMscL (I113L/I70E) gene. Using an OCT (optical coherence tomography) guided continuous wave laser beam, the retina of the eye was irradiated in a spatially controlled manner. Two weeks after the irradiation, mice were sacrificed, their eyes fixed and retina flat-mounts made for immuno-histochemical analysis. Immunostaining with anti-mCherry antibody showed EcMscL (I113L/I70E)-mCherry expression in the treated eye [FIG. 7] and no expression in control eyes.

Example 6

The experiment outlined below demonstrates that EcMscL-mCherry gene (see SEQ ID NO. 1) can be expressed in the mouse brain following intravenous injection of the adeno-associated virus (AAV) carried EcMscL-mCherry gene. Virus was administered through the lateral tail vein. First, a lamp was used to heat the tail and visualize the vein. Then, ~100 µl of virus, a total of ~1×10$^{11}$ vg, was injected into the lateral tail vein (AAV2/8-pMGP-EcMscL-mCherry). Four weeks after the injection, mice were sacrificed, their brains fixed and sectioned for immunohistochemical analysis. Immunostaining with an anti-mCherry antibody showed EcMscL expression at the edge of the cerebellum [FIG. 8A, FIG. 8B] and in the Pons and medulla regions [FIG. 8C, FIG. 8D]. These results demonstrate that virus injected intravenously can cross the blood brain barrier and lead to transduction of MscL expression in the brain.

Example 7

The experiments outlined below demonstrate that *Mycobacterium tuberculosis* MscL (MtMscL) can be expressed and function in mammalian cells and can be used for molecular delivery and osmotic pressure control. The MscL gene from the H37Rv *Mycobacterium tuberculosis* strain, which encodes for a 151 amino acid monomer, was codon optimized for mammalian cell expression, N-terminally fused to a signal peptide and C-terminally fused to mCherry (See SEQ ID NO. 2). The signal peptide was used to target the protein to the plasma membrane and the fluorescent reporter was chosen to act as a visual marker of gene expression and membrane localization. HEK293 cells were transfected with the construct and were cultured in 1 mL of standard DMEM growth media in 35 mm petri dishes. A lipofection agent was used to deliver the plasmid DNA to the cells. Fluorescent confocal microscopy of live cells was used to confirm the successful transfection and expression of the fluorescent reporter linked gene. 560-660 nm red emission filter was used to visualize mCherry fluorescence. A population of MtMscL-mCherry transfected HEK293 cells [FIG. 9A] were fluorescent, thereby indicating that MtMscL can be expressed in mammalian hosts. Additionally, the florescence was predominantly seen in the plasma membrane of the cells, thereby indicated successful membrane targeting by the signal peptide.

MtMscL channel function in mammalian cells was also probed by recording electrophysiological measurements from whole cell patches of HEK293 cells expressing MtMscL-mCherry. The patch-clamp recording setup includes an inverted Nikon fluorescence microscope (TS 100) platform using an amplifier system (Axon Multiclamp 700B, Molecular Devices). Micropipettes were pulled using a two-stage pipette puller (Narshinghe) to attain resistance of 3 to 5 M$\square$ when filled with a solution containing (in mM) 130 K-Gluoconate, 7 KCl, 2 NaCl, 1 MgCl2, 0.4 EGTA, 10 HEPES, 2 ATP-Mg, 0.3 GTP-Tris and 20 sucrose. The micropipette-electrode was mounted on a micromanipulator. The extracellular solution contained (in mM): 150 NaCl, 10 Glucose, 5 KCl, 2 CaCl$_2$), 1 MgCl2 was buffered with 10 mM HEPES (pH 7.3). Currents were measured while holding cells in voltage clamp at −70 mV. The electrophysiological signals from the amplifier were digitized using Digidata 1440 (Molecular devices), interfaced with patch-clamp software (Clampex, Molecular Devices). pClamp 10 software was used for data analysis. Channel activity was induced by subjecting the patched cell to a hypo-osmotic shock by addition of 20-40% v/v water. A stable gigaohm seal was achieved and the current traces show channel activity only after the hypo-osmotic shock [FIG. 9B], demonstrating that the MtMscL channel is functional in mammalian cells.

HEK293 cells expressing MtMscL-mCherry were subjected to a hypo-osmotic shock in the presence of the membrane impermeable dye, Alexa Fluor™ 488 carboxylic acid succinimidyl ester, by the addition of 20-40% water v/v. The cells were then monitored by confocal fluorescence microscopy for 10-25 minutes in red (543 nm excitation and 560-660 nm emission for mCherry) and green (488 nm excitation and detection through a 505-525 nm emission filter for the membrane impermeable dye) channel [FIG. 9C, overlay of green and red channels]. Analysis of fluorescence images show that after hypo-osmotic shock, only red (mCherry) fluorescent MtMscL expressing cells uptake the green impermeable dye [FIG. 9D]. Non-fluorescent cells stay swollen and dark after the osmotic down shock indicating there was no MtMscL activity (i.e. no transport of extra-cellular impermeable dye). Therefore, we can deduce that red fluorescence is correlated with MtMscL activity and that transfection with the MtMscL-mCherry construct led to the expression of a functional membrane-integrated MtMscL-mCherry channel protein capable of osmoregulation and molecular delivery.

Example 8

The experiments outlined below demonstrate that a variant of *E. coli* MscL (EcMscL), EcMscL (I113L/I70E) can be expressed and function in mammalian cells, can be used for molecular delivery and osmotic pressure control and has different gating kinetics from the wild-type channel. The MscL gene from the BL21(DE3) *E. coli* strain, which encodes for a 136 amino acid monomer, was codon optimized for mammalian cell expression, N-terminally fused to a signal peptide, C-terminally fused to mCherry and the I113 and I70 residues mutated (See SEQ ID NO. 5). The signal peptide was used to target the protein to the plasma membrane, the fluorescent reporter was chosen to act as a visual marker of gene expression and membrane localization and the mutations were made to modify channel kinetics. HEK293 cells were transfected with the construct and were cultured in 1 mL of standard DMEM growth media in 35 mm petri dishes. A lipofection agent was used to deliver the plasmid DNA to the cells. Fluorescent confocal microscopy of live cells was used to confirm the successful transfection and expression of the fluorescent reporter linked gene. A 560-660 nm red emission filter was used to visualize mCherry fluorescence. A population of HEK293 cells [FIG. 10A] were fluorescent, thereby indicating that EcMscL (I113L/I70E) can be expressed in mammalian hosts.

EcMscL (I113L/I70E) (See SEQ ID NO. 5) channel function in mammalian cells was probed by recording electrophysiological measurements from whole cell patches of HEK293 cells expressing EcMscL (I113L/I70E)-mCherry. The patch-clamp recording setup includes an inverted Nikon fluorescence microscope (TS 100) platform using an amplifier system (Axon Multiclamp 700B, Molecular Devices). Micropipettes were pulled using a two-stage pipette puller (Narshinghe) to attain resistance of 3 to 5 M☐ when filled with a solution containing (in mM) 130 K-Gluoconate, 7 KCl, 2 NaCl, 1 MgCl2, 0.4 EGTA, 10 HEPES, 2 ATP-Mg, 0.3 GTP-Tris and 20 sucrose. The micropipette-electrode was mounted on a micromanipulator. The extracellular solution contained (in mM): 150 NaCl, 10 Glucose, 5 KCl, 2 $CaCl_2$), 1 MgCl2 was buffered with 10 mM HEPES (pH 7.3). Currents were measured while holding cells in voltage clamp at −70 mV. The electrophysiological signals from the amplifier were digitized using Digidata 1440 (Molecular devices), interfaced with patch-clamp software (Clampex, Molecular Devices). pClamp 10 software was used for data analysis. Channel activity was induced by subjecting the patched cell to a hypo-osmotic shock by addition of 20-40% v/v water. A stable gigaohm seal was achieved and the current traces show channel activity only after the hypo-osmotic shock [FIG. 10B], demonstrating that the EcMscL (I113L/I70E) channel is functional in mammalian cells.

HEK293 cells expressing EcMscL (I113L/I70E)-mCherry (monitored via a red emission filter: 560-660 nm) were subjected to a hypo-osmotic shock in the presence of the membrane impermeable dye, Alexa Fluor™ 488 carboxylic acid succinimidyl ester, by the addition of 20-40% water v/v. The cells were then monitored by confocal fluorescence microscopy for 10-15 minutes at 488 nm excitation and detected through a green emission filter (505-525 nm). Analysis of fluorescence images show that after hypo-osmotic shock, only red fluorescent EcMscL (I113L/I70E) expressing cells uptake the green dye [FIG. 10C]. Non-fluorescent cells stay swollen and dark after the osmotic down shock indicating there was no EcMscL (I113L/I70E) activity (i.e. no transport of extra-cellular impermeable dye). Therefore, we can deduce that red fluorescence is correlated with EcMscL (I113L/I70E) activity and that transfection with the EcMscL (I113L/I70E)-mCherry construct led to the expression of a functional membrane-integrated EcMscL (I113L/I70E)-mCherry channel protein capable of osmoregulation and molecular delivery.

Example 9

The experiments outlined below demonstrate that *Vibrio cholerae* MscL (VcMscL) can be expressed and function in mammalian cells and can be used for molecular delivery and osmotic pressure control. The MscL gene from the O395 *V. cholerae* strain, which encodes for a 136 amino acid monomer, was codon optimized for mammalian cell expression, N-terminally fused to a signal peptide and C-terminally fused to mCherry (See SEQ ID NO. 2). The signal peptide was used to target the protein to the plasma membrane and the fluorescent reporter was chosen to act as a visual marker of gene expression and membrane localization. HEK293 cells were transfected with the construct and were cultured in 1 mL of standard DMEM growth media in 35 mm petri dishes. A lipofection agent was used to deliver the plasmid DNA to the cells. Fluorescent confocal microscopy of live cells was used to confirm the successful transfection and expression of the fluorescent reporter linked gene. The samples were excited at 543 nm and a 560-660 nm red emission filter was used to visualize mCherry fluorescence. A population of HEK293 cells [FIG. 11A] were fluorescent, thereby indicating that VcMscL can be expressed in mammalian hosts. HEK293 cells expressing VcMscL-mCherry (monitored via a red emission filter: 560-660 nm) were subjected to a hypo-osmotic shock in the presence of Alexa Fluor™ 488 carboxylic acid succinimidyl ester by the addition of 20-40% water v/v. The cells were then monitored by confocal fluorescence microscopy for 10-25 minutes at 488 nm excitation and detected through a green emission filter (505-525 nm) [FIG. 11A]. Analysis of fluorescence images show that after hypo-osmotic shock, only red fluorescent VcMscL expressing cells uptake the green dye [FIG. 11B]. Non-fluorescent cells stay swollen and dark after the osmotic down shock indicating there was no VcMscL activity (i.e. no transport of extra-cellular impermeable dye). Therefore, we can deduce that red fluorescence is correlated with VcMscL activity and that transfection with the VcMscL-mCherry construct led to the expression of a functional membrane-integrated VcMscL-mCherry channel protein capable of osmoregulation and molecular delivery.

Example 10

The experiment outlined below demonstrates that EcMscL-mCherry gene (see SEQ ID NO. 1) can be expressed in the mouse blood vessels. In control mice, immunostaining with an anti-mCherry antibody showed no expression of mCherry around blood vessels [FIG. 12A]. EcMscL expression in the boundary of the blood vessels of mice transfected with EcMscL-mCherry (I113L/I70E, SEQ ID No. 5) genes [FIG. 12B]. Such bacterial mechanosensitive channels expressing in blood vessels allows activation by internal or external mechanical stimuli for allowing delivery of therapeutic drugs to the target organ of interest as well as for clearance of toxins. Thus, this method allows removal of Beta-Amyloid, Tau, Alpha-synuclein and PolyQ from central nervous system to the blood stream via the blood brain barrier (BBB), the blood-retinal barrier and the blood-spinal cord barrier in neurodegenerative diseases including but not limited to Alzheimer's, Parkinson's, and Huntington's disease.

Example 11

The experiment outlined below demonstrates that MscL when expressed in mammalian cells, generate burst of electrical activities in hypotonic environment. HEK293 cells were cultured in standard DMEM growth media on multi-electrode array (MEA) petri dishes and a lipofection agent was used to transfect the cells with EcMscL-mCherry gene (I113L/I70E, SEQ ID No. 5) plasmid DNA. Extracellular potential of EcMscL expressing HEK293 cells grown on a multi-electrode array (MEA) petri dish was measured in absence and presence of hypotonic shock (addition of 20% v/v water). Burst of spikes can be seen in the signal during 13-14.5 sec [FIG. 13], demonstrating robust EcMscL channel activities. This result in combination with the result shown in FIG. 4G shows that MscL or their generated site-directed mutants, when expressed in cells act as osmoregulators and generates electrical activities in response to osmotic shocks. Thus, the Hematopoietic stem cells expressing MsCL will generate red blood cells which act as osmoregulators and resistant to osmotic shock, in the treatment and prevention of hyper- as well as hypo-tension related diseases.

Example 12

The experiment outlined below demonstrates that *E. coli* MscL (EcMscL) channel activity can be induced in HEK cells (model for excitatory cells such as neuron and cardiac cells) by ultrasound stimulation. HEK293 cells were cultured in standard DMEM growth media on multi-electrode array (MEA) petri dishes and a lipofection agent was used to transfect the cells with plasmid DNA. The MEA plate was placed on an ultrasound device and was set up to record electrical signals from all electrodes simultaneously. Therefore, any channel activity in cells attached to an electrode would lead to a spike in the electrical signal from that electrode. Ultrasound stimulation (Pulse width: 250 ms, Repetition rate: 2 Hz, Frequency: 1.1 MHz) was used to stimulate the cells on the MEA plate. No electrical activities were observed in control cells (not transfected with EcMscL) stimulated by ultrasound or in EcMscL-transfected cells without ultrasound stimulation [FIG. 14A]. The electrical recordings show a spike in signal on some electrodes after ultrasound stimulation [FIG. 14B]. The results of the experiment confirm that MscL channel activity can be stimulated by ultrasound. Thus, heterologously expressed mechanosensitive channels, such as bacterial mechanosensitive channels or their generated site-directed mutants, in neurons are activated by internal or external mechanical stimuli, for modulating activities in dormant neurons in order to recover from coma, and persistent vegetative state. Thus, heterologously expressed mechanosensitive channels, or their generated site-directed mutants, in neurons can be activated by internal or external mechanical stimuli, for modulating neural activities in order to repair injury such as concussion, enhance neural regeneration, accelerated learning and memory processing. Efficiency of such external stimulation process can be enhanced with or without conjugation of nanoprobes, wherein the device providing external mechanical force or magnetic field can be controlled to tune the duration, frequency and strength of stimulation. This will allow control on molecular delivery, stimulation or cellular death leading to the desired therapeutic outcome.

Example 13

The experiment described below was conducted to test if the mechanosensitive channel (MscL) can be expressed in corneal epithelial cells, so that those cells' activities can be modulated for alleviation of dry eye disease (DED). The mice were treated with intracameral injection of adeno-associated virus containing the EcMscL-mCherry gene (AAV2/8-EcMscL-mCherry, $6.75 \times 10^{10}$ vg/eye) into the anterior chamber of the eye. The needle was inserted through the cornea, anterior to the iridocorneal angle, and 3 µl of virus was pumped into the eye at a rate of 1 µl/min. The needle was left in place in the eye for 1 min after injection and then slowly retracted. FIG. 15 shows the confocal Image of a section of the mouse cornea transfected with EcMscL-mCherry. Expression of reporter-mCherry exhibited red fluorescence, detected by 543 nm excitation and 560-660 nm emission. Using this viral transduction method, meibomian glands endothelial cells can also be made to express MscL, which can be stimulated mechanically (as demonstrated in model HEK cells in FIG. 14B) that would lead to enhance in secretion of aqueous phase of the tear film and thus, alleviation of dry eye disease (DED).

Example 14

The example described below demonstrates that MscL-mCherry gene can be expressed in the heart and other vital organs such as the kidney in order to allow modulation of cellular function and associated therapeutic outcome. The adeno-associated virus (AAV) carried EcMscL-mCherry gene was administered through the lateral tail vein. First, a lamp was used to heat the tail and visualize the vein. Then, ~100 µl of virus, a total of $\sim 1 \times 10^{11}$ vg, was injected into the lateral tail vein. Four weeks after the injection, mice were sacrificed, their hearts and kidneys fixed and sectioned for immunohistochemical analysis. Immunostaining with an anti-mCherry antibody showed EcMscL expression in the heart [FIG. 16A]. FIG. 16B shows confocal Image of the mouse kidney transfected with EcMscL-mCherry via AAV based gene transduction. Expression of reporter-mCherry exhibited by characteristic red fluorescence in 560-660 nm emission band. Thus, the cardiac or kidney cells expressing mechanosensitive channels (e.g., MscL) or their generated site-directed mutants can be activated by internal or external mechanical stimuli, and used as osmoregulators or diuretics in the renal system for the treatment and prevention of kidney stones and chronic kidney disease.

Example 15

The example described below demonstrates that MscL-mCherry gene can be expressed in the liver in order to allow modulation of cellular function and associated therapeutic outcome. To achieve transduction in the liver, the adeno-associated virus (AAV) carried EcMscL-mCherry gene was administered through the lateral tail vein. First, a lamp was used to heat the tail and visualize the vein. Then, ~100 µl of virus, a total of $\sim 1 \times 10^{11}$ vg, was injected into the lateral tail vein. Four weeks after the injection, mice were sacrificed, their livers fixed and sectioned for immunohistochemical analysis. Immunostaining with an anti-mCherry antibody showed EcMscL expression in the liver [FIG. 16C] transfected with EcMscL-mCherry via AAV based gene transduction. Expression of reporter-mCherry exhibited by characteristic red fluorescence. The heterologously expressed mechanosensitive channels, such as bacterial mechanosensitive channels (MscL), or their generated site-directed mutants expressed in liver, gallbladder or bile duct cells of the hepatic system can thus be used as bile regulators, activated by internal or external mechanical stimuli for the treatment and prevention of gallstones.

Example 16

The example described below demonstrates that MscL-mCherry gene can be expressed in the lung in order to allow modulation of cellular function and associated therapeutic outcome. To achieve transduction in the lung, the adeno-associated virus (AAV) carried EcMscL-mCherry gene was administered through the lateral tail vein. First, a lamp was used to heat the tail and visualize the vein. Then, ~100 µl of virus, a total of $\sim 1 \times 10^{11}$ vg, was injected into the lateral tail vein. Four weeks after the injection, mice were sacrificed, their lungs fixed and sectioned for immunohistochemical analysis. Immunostaining with an anti-mCherry antibody showed EcMscL expression in the lung [FIG. 16D] transfected with EcMscL-mCherry via AAV based gene transduction. Expression of reporter-mCherry exhibited by red fluorescence. The mechanosensitive channels, such as bacterial mechanosensitive channels (MscL), or their generated site-directed mutants, heterologously expressed in Pneumocytes, can be used as ports for exchange of oxygen and Carbon dioxide from alveolus to the blood capillaries and vice a versa. The activities of these channels/ports on Pneumocytes can be further modulated by internal or external mechanical stimuli for treatment of lung diseases including but not limited to Black Lung Disease (Coal workers' pneumoconiosis).

TABLE-01

Amino acid sequence of a synthetic mechanosensitive channel derived from *Escherichia Coli* -MscL with signaling peptides for mammalian plasma membrane targeting.

Met Leu Pro Gln Gln Val Gly Phe Val Cys Ala Val Leu Ala Leu Val Cys Cys Ala Ser Gly Met Ser
Ile Ile Lys Glu Phe Arg Glu Phe Ala Met Arg Gly Asn Val Val Asp Leu Ala Val Gly Val Ile Ile Gly
Ala Ala Phe Gly Lys Ile Val Ser Ser Leu Val Ala Asp Ile Ile Met Pro Pro Leu Gly Leu Leu Ile Gly
Gly Ile Asp Phe Lys Gln Phe Ala Val Thr Leu Arg Asp Ala Gln Gly Asp Ile Pro Ala Val Val Met His
Tyr Gly Val Phe Ile Gln Asn Val Phe Asp Phe Leu Ile Val Ala Phe Ala Ile Phe Met Ala Ile Lys
Leu Ile Asn Lys Leu Asn Arg Lys Lys Glu Glu Pro Ala Ala Ala Pro Ala Pro Thr Lys Glu Glu Val
Leu Leu Thr Glu Ile Arg Asp Leu Leu Lys Glu Gln Asn Asn Arg Ser (SEQ ID No: 1)

TABLE-02

Amino acid sequence of a synthetic mechanosensitive channel derived from *Mycobacterium Tuberculosis* - MscL with signaling peptides for mammalian plasma membrane targeting.

Met Leu Pro Gln Gln Val Gly Phe Val Cys Ala Val Leu Ala Leu Val Cys Cys Ala Ser Gly Met Leu
Lys Gly Phe Lys Glu Phe Leu Ala Arg Gly Asn Ile Val Asp Leu Ala Val Ala Val Val Ile Gly Thr Ala
Phe Thr Ala Leu Val Thr Lys Phe Thr Asp Ser Ile Ile Thr Pro Leu Ile Asn Arg Ile Gly Val Asn Ala
Gln Ser Asp Val Gly Ile Leu Arg Ile Gly Ile Gly Gly Gly Gln Thr Ile Asp Leu Asn Val Leu Leu Ser
Ala Ala Ile Asn Phe Phe Leu Ile Ala Phe Ala Val Tyr Phe Leu Val Val Leu Pro Tyr Asn Thr Leu
Arg Lys Lys Gly Glu Val Glu Gln Pro Gly Asp Thr Gln Val Val Leu Leu Thr Glu Ile Arg Asp Leu
Leu Ala Gln Thr Asn Gly Asp Ser Pro Gly Arg His Gly Gly Arg Gly Thr Pro Ser Pro Thr Asp Gly
Pro Arg Ala Ser Thr Glu Ser Gln (SEQ ID No: 2)

TABLE-03

Amino acid sequence of a synthetic mechanosensitive channel derived from *Staphylococcus aureus* - MscL with signaling peptides for mammalian plasma membrane targeting.

Met Leu Pro Gln Gln Val Gly Phe Val Cys Ala Val Leu Ala Leu Val Cys Cys Ala Ser Gly Met Leu
Lys Glu Phe Lys Glu Phe Ala Leu Lys Gly Asn Val Leu Asp Leu Ala Ile Ala Val Val Met Gly Ala
Ala Phe Asn Lys Ile Ile Ser Ser Leu Val Glu Asn Ile Ile Met Pro Leu Ile Gly Lys Ile Phe Gly Ser
Val Asp Phe Ala Lys Glu Trp Ser Phe Trp Gly Ile Lys Tyr Gly Leu Phe Ile Gln Ser Val Ile Asp Phe
Ile Ile Ile Ala Phe Ala Leu Phe Ile Phe Val Lys Ile Ala Asn Thr Leu Met Lys Lys Glu Glu Ala Glu
Glu Glu Ala Val Val Glu Glu Asn Val Val Leu Leu Thr Glu Ile Arg Asp Leu Leu Arg Glu Lys Lys
(SEQ ID No: 3)

TABLE-04

Amino acid sequence of a synthetic mechanosensitive channel derived from *Vibrio cholerae*-MscL with signaling peptides for mammalian plasma membrane targeting.

Met Leu Pro Gln Gln Val Gly Phe Val Cys Ala Val Leu Ala Leu Val Cys Cys Ala Ser Gly Met Ser
Leu Leu Lys Glu Phe Lys Ala Phe Ala Ser Arg Gly Asn Val Ile Asp Met Ala Val Gly Ile Ile Ile Gly

TABLE-04-continued

Amino acid sequence of a synthetic mechanosensitive channel derived from *Vibrio cholerae*-MscL with signaling peptides for mammalian plasma membrane targeting.

Ala Ala Phe Gly Lys Ile Val Ser Ser Phe Val Ala Asp Ile Ile Met Pro Pro Ile Gly Ile Ile Leu Gly

Gly Val Asn Phe Ser Asp Leu Ser Phe Val Leu Leu Ala Ala Gln Gly Asp Ala Pro Ala Val Val Ile

Ala Tyr Gly Lys Phe Ile Gln Thr Val Val Asp Phe Thr Ile Ile Ala Phe Ala Ile Phe Met Gly Leu Lys

Ala Ile Asn Ser Leu Lys Arg Lys Glu Glu Glu Ala Pro Lys Ala Pro Pro Ala Pro Thr Lys Asp Gln

Glu Leu Leu Ser Glu Ile Arg Asp Leu Leu Lys Ala Gln Gln Asp Lys (SEQ ID No: 4)

TABLE-05

Amino acid sequence of a synthetic mechanosensitive channel derived from *Escherichia Coli*-MscL with signaling peptides for mammalian plasma membrane targeting having mutation (|113L/170E).

Met Leu Pro Gln Gln Val Gly Phe Val Cys Ala Val Leu Ala Leu Val Cys Cys Ala Ser Gly Met Ser

Ile Ile Lys Glu Phe Arg Glu Phe Ala Met Arg Gly Asn Val Val Asp Leu Ala Val Gly Val Ile Ile Gly

Ala Ala Phe Gly Lys Ile Val Ser Ser Leu Val Ala Asp Ile Ile Met Pro Pro Leu Gly Leu Leu Glu Gly

Gly Ile Asp Phe Lys Gln Phe Ala Val Thr Leu Arg Asp Ala Gln Gly Asp Ile Pro Ala Val Val Met His

Tyr Gly Val Phe Ile Gln Asn Val Phe Asp Phe Leu Ile Val Ala Phe Ala Leu Phe Met Ala Ile Lys

Leu Ile Asn Lys Leu Asn Arg Lys Lys Glu Glu Pro Ala Ala Ala Pro Ala Pro Thr Lys Glu Glu Val

Leu Leu Thr Glu Ile Arg Asp Leu Leu Lys Glu Gln Asn Asn Arg Ser (SEQ ID No: 5)

TABLE-06

Amino acid sequence of a synthetic mechanosensitive channel derived from *Escherichia Coli*-MscL with signaling peptides for mammalian plasma membrane targeting having mutation (|113L/K122T).

Met Leu Pro Gln Gln Val Gly Phe Val Cys Ala Val Leu Ala Leu Val Cys Cys Ala Ser Gly Met Ser

Ile Ile Lys Glu Phe Arg Glu Phe Ala Met Arg Gly Asn Val Val Asp Leu Ala Val Gly Val Ile Ile Gly

Ala Ala Phe Gly Lys Ile Val Ser Ser Leu Val Ala Asp Ile Ile Met Pro Pro Leu Gly Leu Leu Ile Gly

Gly Ile Asp Phe Lys Gln Phe Ala Val Thr Leu Arg Asp Ala Gln Gly Asp Ile Pro Ala Val Val Met His

Tyr Gly Val Phe Ile Gln Asn Val Phe Asp Phe Leu Ile Val Ala Phe Ala Leu Phe Met Ala Ile Lys

Leu Ile Asn Thr Leu Asn Arg Lys Lys Glu Glu Pro Ala Ala Ala Pro Ala Pro Thr Lys Glu Glu Val

Leu Leu Thr Glu Ile Arg Asp Leu Leu Lys Glu Gln Asn Asn Arg Ser (SEQ ID No: 6)

The specification and examples herein provide a complete description of the structure and use of illustrative embodiments. Although certain embodiments have been described with a certain degree of particularity, or with reference to one or more individual embodiments, those skilled in the art could make numerous alterations to the disclosed embodiments without departing from the scope of this invention. As such, the various illustrative embodiments of the devices are not intended to be limited to the particular forms disclosed. Rather, they include all modifications and alternatives falling within the scope of the claims, and embodiments other than the one shown may include some or all of the features of the depicted embodiment. For example, components may be omitted or combined as a unitary structure, and/or connections may be substituted. Further, where appropriate, aspects of any of the examples described above may be combined with aspects of any of the other examples described to form further examples having comparable or different properties and addressing the same or different problems. Similarly, it will be understood that the benefits and advantages described above may relate to one embodiment or may relate to several embodiments.

While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the present invention.

Furthermore, the claims are not intended to include, and should not be interpreted to include, means-plus- or step-plus-function limitations, unless such a limitation is explicitly recited in a given claim using the phrase(s) "means for" or "step for," respectively.

Clauses

It will be understood that the following clauses form part of the disclosure of the invention defined herein. More particularly, the invention herein may be defined by the combination of the features of the clauses as detailed below, and said clauses may be utilized to amend the combination of the features within the claims of this application.

1. A synthetic polypeptide sequence of MscL1 protein and its generated site-directed mutants comprising: an MscL1 protein that, when expressed on mammalian cell membrane, senses pressure changes and modulates the intra-cellular pressure, or molecular transport not limited to aqueous fluid and therapeutic molecules, wherein the MscL1 protein has SEQ ID NO: 1.

2. The protein of clause 1, wherein one or more of a single or combination of mutations modulate pressure sensitivity, pore size, gating, or kinetics, wherein the mutation and/or deletion is selected from but not limited to:

I to L substitution at an amino acid residue corresponding to amino acid I at position 113 of the MscL sequence (SEQ ID No. 1) sensitizes sonic response activated by ultrasound at a very low pressure;

A to H or C substitution at an amino acid residue corresponding to amino acid A at position 131 of the MscL (SEQ ID No. 1) to modulate the pore size of the MscL channel to control the size of molecules that can be transported via the channels;

A to H or C substitution at an amino acid residue corresponding to amino acid A at position 133 of the MscL (SEQ ID No. 1) to modulate the size of the MscL nanovalve to control diffusion and active transport via said nanovalves;

G to any other 19 naturally occurring amino acid substitution at an amino acid residue corresponding to amino acid G at position 43 of the MscL (SEQ ID No. 1) leads to hypersensitivity to stretch forces that are activated at low threshold and an increase in pressure sensitivity;

I to any other 19 naturally occurring amino acid substitution at an amino acid residue corresponding to amino acid I at position 70 of the MscL (SEQ ID No. 1) in order to control MscL channel kinetics as well as mechanosensitivity;

V to C amino acid substitution at an amino acid residue corresponding to amino acid V at position 44 of the MscL (SEQ ID No. 1) to increase the pressure sensitivity and shorten open times;

K to D or E amino acid substitution at an amino acid residue corresponding to amino acid K at position 52 of the MscL (SEQ ID No 1) for increased pressure sensitivity and shortening mean open times and lowering a transition barrier;

Q to C or P or F or W or Y or H amino acid substitution at an amino acid residue corresponding to amino acid Q at position 77 of the MscL (SEQ ID No 1) for increased pressure sensitivity and shortening mean open times and lowering transition barrier; L to C amino acid substitution at an amino acid residue corresponding to amino acid L at position 40 of the MscL (SEQ ID No. 1) for increasing sensitivity to a higher gating threshold;

K to any negatively charged amino acid substitution at an amino acid residue corresponding to amino acid K at position 122 of the MscL SEQ ID No. 1 to tune MscL channel mechanosensitivity and kinetics;

D to any amino acid substitution at an amino acid residue corresponding to amino acid D at 39 or position 42 of the MscL SEQ ID No. 1 for functional alterations; and deletion of amino acid(s) from position(s) 131 to 133, 131 to 136 or 131 to 157 of the MscL SEQ ID No. 1 for increasing the pressure sensitivity and shortening open times.

3. A synthetic polypeptide sequence of MscL2 protein and its generated site-directed mutants comprising: an MscL2 protein that, when expressed on mammalian cell membrane, senses pressure changes and modulates the intra-cellular pressure, or molecular transport not limited to aqueous fluid and therapeutic molecules, wherein the MscL2 protein has SEQ ID NO: 2.

4. A synthetic polypeptide sequence of MscL3 protein and its generated site-directed mutants comprising: an MscL3 protein that, when expressed on mammalian cell membrane, senses pressure changes and modulates the intra-cellular pressure, or molecular transport not limited to aqueous fluid and therapeutic molecules, wherein the MscL3 protein has SEQ ID NO: 3.

5. A synthetic polypeptide sequence of MscL4 protein and its generated site-directed mutants comprising: an MscL4 protein that, when expressed on mammalian cell membrane, senses pressure changes and modulates the intra-cellular pressure, or molecular transport not limited to aqueous fluid and therapeutic molecules, wherein the MscL4 protein has SEQ ID NO: 4.

6. A synthetic polypeptide sequence of any of clauses 1-5 wherein one or more of MscL protein(s) or chimera of sequence elements of different MscL protein(s) or concatemers of MscL monomers expressed in a cell is fused to one or more amino acid sequence motifs selected from the group consisting of a signal peptide, an endoplasmic reticulum (ER) export signal, a membrane trafficking signal, and an N-terminal Golgi export signal. Specifically, the signal consists of MLPQQVGFVCAVLALVCCASG, optionally wherein the signaling sequence is selected from MGRLLA-LVVGAALVSSAC or MAVPARTCGASRPGPART or any signaling peptide sequences.

7. The protein of any of clauses 1-6 for use in a method wherein heterologously expressed mechanosensitive channels, optionally including bacterial mechanosensitive channels optionally including MscL, MscS, MscK, or MscG, plant mechanosensitive channels (MSL2-10), TRPV1-TRPV5 channels, Piezo channels or their generated site-directed mutants are used as a tension activated pressure release valve in cells including trabeculocytes, epithelial cells and other cells of the body that are subjected to mechanical or osmotic pressure for therapeutic purpose.

8. The protein of clause 7 wherein the MscL homologues strains includes but is not limited to MscLs from *Escherichia coli, Mycobacterium Tuberculosis, Vibrio cholera, Bacillus subtilis, Mycobacterium leprae, Chlorobium tepidum, Thermus thermophilus, Haemophilus influenza, Erwinia carotovora, Pseudomonas fluorescens, Clostridium perfringens, Staphylococcus aureus, Streptococcus faecalis, Lactococcus lactis, Brucella melitensis, Caulobacter cres-*

*centus, Clostridium histolyticum, Fusobacterium nucleatum* subsp, *Mesorhizobium loti, Pasteurella multocida, Pectobacterium carotovorum, Pseudomonas aeruginosa, Salmonella enterica serovar Typhimurium, Salmonella enterica serovar Typhi, Xylella fastidiosa, Corynebacterium glutamicum, Deinococcus radiodurans, Lactococcus lactis, Ralstonia solanacearum, Sinorhizobium meliloti, Streptococcus pneumoniae, Streptococcus pyogenes, Streptomyces coelicolor, Methanosarcina acetivorans Listeria innocua, Listeria monocytogenes.*

9. The protein of clause 7, wherein the said mechanosensitive channel (e.g., MscL) is delivered through viral vectors or non-viral methods and said channel acts as a transgenic pressure modulator in the impaired cells of glaucomatous eyes in selected but not limited to Trabecular Meshwork (TM) cells by use of promoters optionally including a matrix Gla protein (MGP) promoter.

10. The protein of clause 9, where in the said viral vectors is selected from but not limited to, adeno virus, adeno associated-virus, lentivirus; and the non-viral method for delivery of the mechanosensitive channel promoting gene to the targeted site(s) is selected from but not limited to physical methods optionally including light, laser, ultrasound, or electric field, or chemical methods optionally including Lipid carrier, or DEAA-Dextran.

11. The protein of clause 7, wherein the said mechanosensitive channel functions as an alternative outflow actuator and supplements native paracytosis and transcytosis in the movement of aqueous humor through the endothelial cells of the TM, thereby alleviating outflow resistance and lowering of IOP for the treatment of POAG (Primary Open-Angle Glaucoma).

12. The protein of clause 7, wherein, the said mechanosensitive channel, its variants, and the generated site-directed mutants are activated at selected but not limited to physiological and non-physiological pressures such as greater than 20 mmHg in an eye; or 120-200 mmHg (systolic) and 80-110 (diastolic) in artery; or greater than 15 mmHg intracranial pressure.

13. The protein of clause 7, wherein the said mechanosensitive channel, its variants and the generated site-directed mutants are activated at the targeted site with the aid of external devices optionally including ultrasound actuation or other physical perturbations.

14. The protein of clause 7, wherein in the expression of the said mechanosensitive channel in corneal epithelial cells with or without mechanical stimulation enhances secretion of aqueous phase of the tear film to alleviate of dry eye disease (DED).

15. The protein of clause 7, wherein heterologously expressed mechanosensitive channels, optionally including bacterial mechanosensitive channels optionally including MscL, MscS, MscK, or MscG, plant mechanosensitive channels (MSL2-10), TRPV1-TRPV5 channels, Piezo channels or their generated site-directed mutants are used as osmoregulators, activated by internal or external mechanical stimuli, in the epithelial cells of the arterial system in the treatment and prevention of hypo- as well as hyper-tension.

16. The protein of clause 7, wherein the mechanosensitive channels, optionally including bacterial mechanosensitive channels optionally including MscL, MscS, MscK, or MscG, plant mechanosensitive channels (MSL2-10), TRPV1-TRPV5 channels, Piezo channels or their generated site-directed mutants, when expressed in the Hematopoietic stem cells, generates red blood cells which act as osmoregulators and resistant to osmotic shock, in the treatment and prevention of hyper- as well as hypo-tension related diseases.

17. The protein of clause 7, wherein heterologously expressed mechanosensitive channels, optionally including bacterial mechanosensitive channels optionally including MscL, MscS, MscK, or MscG, plant mechanosensitive channels (MSL2-10), TRPV1-TRPV5 channels, Piezo channels or their generated site-directed mutants are used as osmoregulators or diuretics, activated by internal or external mechanical stimuli, in the renal system in the treatment and prevention of kidney stones and chronic kidney disease.

18. The protein of clause 7, wherein heterologously expressed mechanosensitive channels, optionally including bacterial mechanosensitive channels optionally including MscL, MscS, MscK, or MscG, plant mechanosensitive channels (MSL2-10), TRPV1-TRPV5 channels, Piezo channels or their generated site-directed mutants are used as bile regulators, activated by internal or external mechanical stimuli, in liver, gallbladder or bile duct cells of the hepatic system in the treatment and prevention of gallstones.

19. The protein of clause 7, wherein heterologously expressed mechanosensitive channels, optionally including bacterial mechanosensitive channels optionally including MscL, MscS, MscK, or MscG, plant mechanosensitive channels (MSL2-10), TRPV1-TRPV5 channels, Piezo channels or their generated site-directed mutants, are used as osmoregulators, activated by internal or external mechanical stimuli, and alternative outflow/inflow pathway for fluid in the treatment and prevention of edemas, which diseases optionally include, but are not limited to, passive subretinal, cystoid macular, lymph-, peripheral, pulmonary, and pedal edemas as well as osteoarthritis related swollen knees and joints.

20. The protein of clause 7, wherein heterologously expressed mechanosensitive channels, optionally including bacterial mechanosensitive channels optionally including MscL, MscS, MscK, or MscG, plant mechanosensitive channels (MSL2-10), TRPV1-TRPV5 channels, Piezo channels or their generated site-directed mutants, in reproductive system are used as osmoregulators, and alternative outflow/inflow pathway for fluid, activated by internal or external mechanical stimuli, in the treatment and prevention of erectile dysfunction, vaginal dryness, benign prostatic hyperplasia and polycystic ovary syndrome.

21. The protein of clause 7, wherein heterologously expressed mechanosensitive channels, optionally including bacterial mechanosensitive channels optionally including MscL, MscS, MscK, or MscG, plant mechanosensitive channels (MSL2-10), TRPV1-TRPV5 channels, Piezo channels or their generated site-directed mutants, are used as osmoregulators, activated by internal or external mechanical stimuli, and alternative outflow/inflow pathway for fluid in the treatment of any skin related diseases optionally including dysfunction of sweat glands.

22. The protein of clause 7, wherein heterologously expressed mechanosensitive channels, optionally including bacterial mechanosensitive channels optionally including MscL, MscS, MscK, or MscG), plant mechanosensitive channels (MSL2-10), TRPV1-TRPV5 channels, Piezo channels or their generated site-directed mutants, are used as macromolecular pressure release valves, activated by internal or external mechanical stimuli, and alternative outflow pathway for fluid in the treatment of idiopathic intracranial hypertension.

23. The protein of clause 7, wherein heterologously expressed mechanosensitive channels, optionally including bacterial mechanosensitive channels optionally including MscL, MscS, MscK, or MscG, plant mechanosensitive channels (MSL2-10), TRPV1-TRPV5 channels, Piezo channels or their generated site-directed mutants are used as transmembrane ports in cells activated by internal or external mechanical stimuli for enhanced drug delivery in order to increase efficacy of the treatment for diseases including cancer.

24. The protein of clause 7, where in the expression of said mechanosensitive channel in cancer cells, targeted by specific receptors optionally including EGFR, or pH environment, is used to precipitate cell death by either bioengineering a constitutively open a leaky channel or through overstimulation of the channel.

25. The protein of clause 7, wherein heterologously expressed mechanosensitive channels, optionally including bacterial mechanosensitive channels optionally including MscL, MscS, MscK, or MscG, plant mechanosensitive channels (MSL2-10), TRPV1-TRPV5 channels, Piezo channels or their generated site-directed mutants, are used for stimulation of cells, including neurons, cardiac and muscle cells for treatment and prevention diseases optionally including but not limited to, neurological diseases such as pain, epilepsy, stroke as well as cardiovascular diseases and muscular dystrophies.

26. The protein of clause 7, wherein heterologously expressed mechanosensitive channels, optionally including bacterial mechanosensitive channels optionally including MscL, MscS, MscK, or MscG, plant mechanosensitive channels (MSL2-10), TRPV1-TRPV5 channels, Piezo channels or their generated site-directed mutants, in neurons are activated by internal or external mechanical stimuli, for modulating neural activities in order to repair injury optionally including concussion, enhance neural regeneration, accelerated learning and memory processing.

27. The protein of clause 7, wherein heterologously expressed mechanosensitive channels, optionally including bacterial mechanosensitive channels optionally including MscL, MscS, MscK, or MscG, plant mechanosensitive channels (MSL2-10), TRPV1-TRPV5 channels, Piezo channels or their generated site-directed mutants, in neurons are activated by internal or external mechanical stimuli, for modulating activities in dormant neurons in order to recover from coma, and persistent vegetative state.

28. The protein of clause 7, wherein heterologously expressed mechanosensitive channels, optionally including bacterial mechanosensitive channels optionally including MscL, MscS, MscK, or MscG, plant mechanosensitive channels (MSL2-10), TRPV1-TRPV5 channels, Piezo channels or their generated site-directed mutants are used as osmoregulators, activated by internal or external mechanical stimuli, in the central nervous system (ONS) mediated barbers such as blood-cerebrospinal fluid (CSF) barrier, the blood brain barrier (BBB), the blood-retinal barrier and the blood-spinal cord barrier.

29. The protein of clause 7, wherein heterologously expressed mechanosensitive channels, optionally including bacterial mechanosensitive channels optionally including MscL, MscS, MscK, or MscG, plant mechanosensitive channels (MSL2-10), TRPV1-TRPV5 channels, Piezo channels or their generated site-directed mutants, activated by internal or external mechanical stimuli, are used as efflux ports for allowing the clearance of toxins such as Beta-Amyloid, Tau, Alpha-synuclein and PolyQ from central nervous system to the blood stream via the blood brain barrier (BBB), the blood-retinal barrier and the blood-spinal cord barrier in neurodegenerative diseases optionally including but not limited to Alzheimer's, Parkinson's; and Huntington's disease.

30. The protein of clause 7, wherein mechanosensitive channels, optionally including bacterial mechanosensitive channels optionally including MscL, MscS, MscK, or MscG, plant mechanosensitive channels (MSL2-10), TRPV1-TRPV5 channels, Piezo channels or their generated site-directed mutants, heterologously expressed in Pneumocytes, activated by internal or external mechanical stimuli, are used as ports for exchange of oxygen and Carbon dioxide from alveolus to the blood capillaries and vice a versa via the Pneumocytes in lung diseases optionally including but not limited to Black Lung Disease (Coal workers' pneumoconiosis).

31. The protein of clause 7, wherein the cells expressing the mechanosensitive channels optionally including bacterial mechanosensitive channels optionally including MscL, MscS, MscK, or MscG, plant mechanosensitive channels (MSL2-10), TRPV1-TRPV5 channels, Piezo channels or their generated site-directed mutants, with or without fusion or conjugation of nanoprobes, are activated by a device providing external mechanical force or magnetic field, whose duration, frequency and strength is tunable for controlled stimulation, molecular delivery or cellular death leading to the desired therapeutic outcome.

What is claimed is:

1. A synthetic polypeptide sequence of a mechanosensitive channel of large conductance 1 (MscL1) protein and its generated site-directed mutant(s) thereof, wherein said MscL1 or mutant(s) thereof comprises at least 95% sequence identity to SEQ ID NO:1 and wherein the MscL1 protein or mutant(s) thereof, when expressed on mammalian cell membrane, senses pressure changes and modulates the intra-cellular pressure, or molecular transport including aqueous fluid and therapeutic molecules.

2. The synthetic polypeptide sequence of claim 1, wherein said mutant(s) has the function to modulate pressure sensitivity, pore size, gating, or kinetics and is selected from one or more substitutions, deletions or combinations thereof.

3. The synthetic polypeptide sequence of claim 1, wherein said MscL1 or mutant(s) thereof are configured to be a single protein, a concatemer of said MscL1 proteins or mutants thereof.

4. The synthetic polypeptide sequence of claim 1, for use in a method wherein heterologously expressed mechanosensitive channels, its variants, and the generated site-directed mutants thereof, optionally further including bacterial mechanosensitive channels, plant mechanosensitive channels (MSL2-10), TRPV1-TRPV5 channels, Piezo channels or their generated site-directed mutants derived from alternative strains, are used as a tension activated pressure release valve in cells including trabeculocytes, epithelial cells and other cells of the body that are subjected to mechanical or osmotic pressure for a therapeutic purpose.

5. The protein synthetic polypeptide sequence of claim 4, wherein the MscL proteins are derived from alternative strains and comprise at least one selected from MscLs from *Escherichia coli*, *Mycobacterium tuberculosis*, *Vibrio cholera*, *Bacillus subtilis*, *Mycobacterium leprae*, *Chlorobium tepidum*, *Thermus thermophilus*, *Haemophilus influenza*, *Erwinia carotovora*, *Pseudomonas fluorescens*, *Clostridium perfringens*, *Staphylococcus aureus*, *Streptococcus faecalis*, *Lactococcus lactis*, *Brucella melitensis*, *Caulobacter crescentus*, *Clostridium histolyticum*, *Fusobacterium nucleatum* subsp, *Mesorhizobium loti*, *Pasteurella multocida*, *Pectobacterium carotovorum*, *Pseudomonas aeruginosa*, *Salmonella enterica* serovar *Typhimurium*, *Salmonella enterica* serovar *Typhi*, *Xylella fastidiosa*, *Corynebacterium glutamicum*, *Deinococcus radiodurans*, *Lactococcus lactis*, *Ralstonia solanacearum*, *Sinorhizobium meliloti*, *Streptococcus pneumoniae*, *Streptococcus pyogenes*, *Streptomyces coelicolor*, *Methanosarcina acetivorans Listeria innocua*, or *Listeria monocytogenes*.

6. The synthetic polypeptide sequence of claim 4, wherein said mechanosensitive channel is delivered through viral vectors or non-viral methods and said channel acts as a transgenic pressure modulator in the impaired cells of glaucomatous eyes in selected but not limited to Trabecular Meshwork (TM) cells by use of promoters optionally including a matrix Gla protein (MGP) promoter.

7. The synthetic polypeptide sequence of claim 6, wherein said viral vectors are at least one selected from adeno virus, adeno associated-virus, lentivirus; and the non-viral method for delivery of the mechanosensitive channel promoting gene to the targeted site(s) is selected from physical methods optionally including light, laser, ultrasound, or electric field, or chemical methods optionally including Lipid carrier, or DEAA-Dextran.

8. The synthetic polypeptide sequence of claim 4, wherein said mechanosensitive channels function as an alternative outflow actuator and supplements native paracytosis and transcytosis in the movement of aqueous humor through the endothelial cells of the TM, thereby alleviating outflow resistance and lowering of IOP for the treatment of POAG (Primary Open-Angle Glaucoma).

9. The synthetic polypeptide sequence of claim 4, wherein the said mechanosensitive channel, its variants, and the generated site-directed mutants thereof are activated at selected from at least one of physiological and non-physiological pressures selected from at least one of greater than 20 mmHg in an eye; or 120-200 mmHg systolic in an artery and 80-110 mmHg diastolic in an artery; or greater than 15 mmHg intracranial pressure.

10. The synthetic polypeptide sequence of claim 4, wherein the said mechanosensitive channels, its variants and the generated site-directed mutants are activated at the targeted site with the aid of external devices optionally including ultrasound actuation or other physical perturbations.

11. The synthetic polypeptide sequence of claim 4, wherein in the expression of the said mechanosensitive channels, its variants, and the generated site-directed mutants thereof is in corneal epithelial cells with or without mechanical stimulation enhances secretion of aqueous phase of the tear film to alleviate dry eye disease (DED).

12. The synthetic polypeptide sequence of claim 4, wherein heterologously expressed mechanosensitive channels, its variants, and the generated site-directed mutants thereof, optionally including bacterial mechanosensitive channels, optionally including MscL, MscS, MscK, or MscG, plant mechanosensitive channels (MSL2-10), TRPV1-TRPV5 channels, Piezo channels or their generated site-directed mutants for use as osmoregulators, are activated by internal or external mechanical stimuli in the epithelial cells of the arterial system in the treatment and prevention of hypo- as well as hyper-tension.

13. The synthetic polypeptide sequence of claim 4, wherein the mechanosensitive channels, its variants, and the generated site-directed mutants thereof, optionally including bacterial mechanosensitive channels, plant mechanosensitive channels (MSL2-10), TRPV1-TRPV5 channels, Piezo channels or their generated site-directed mutants, when expressed in the Hematopoietic stem cells, generates red blood cells which act as osmoregulators and resistant to osmotic shock, in the treatment and prevention of hyper- as well as hypo-tension related diseases.

14. The synthetic polypeptide sequence of claim 4, wherein heterologously expressed mechanosensitive channels, its variants, and the generated site-directed mutants thereof, optionally including bacterial mechanosensitive channels, plant mechanosensitive channels (MSL2-10), TRPV1-TRPV5 channels, Piezo channels or their generated site-directed mutants for use as osmoregulators or diuretics, are activated by internal or external mechanical stimuli in the renal system in the treatment and prevention of kidney stones and chronic kidney disease.

15. The synthetic polypeptide sequence of claim 4, wherein heterologously expressed mechanosensitive channels, its variants, and the generated site-directed mutants thereof, optionally including bacterial mechanosensitive channels, plant mechanosensitive channels (MSL2-10), TRPV1-TRPV5 channels, Piezo channels or their generated site-directed mutants for use as bile regulators, are activated by internal or external mechanical stimuli, in liver, gallbladder or bile duct cells of the hepatic system in the treatment and prevention of gallstones.

16. The synthetic polypeptide sequence of claim 4, wherein heterologously expressed mechanosensitive channels, its variants, and the generated site-directed mutants thereof, optionally including bacterial mechanosensitive channels, plant mechanosensitive channels (MSL2-10), TRPV1-TRPV5 channels, Piezo channels or their generated site-directed mutants, for use as osmoregulators, are activated by internal or external mechanical stimuli, and alternative outflow/inflow pathway for fluid in the treatment and prevention of edemas, which diseases optionally include passive subretinal, cystoid macular, lymph-, peripheral, pulmonary, pedal edemas, and osteoarthritis related swollen knees and joints.

17. The synthetic polypeptide sequence of claim 4, wherein heterologously expressed mechanosensitive channels, its variants, and the generated site-directed mutants thereof, optionally including bacterial mechanosensitive channels, plant mechanosensitive channels (MSL2-10), TRPV1-TRPV5 channels, Piezo channels or their generated site-directed mutants, in reproductive system for use as osmoregulators, and alternative outflow/inflow pathway for fluid, are activated by internal or external mechanical stimuli, in the treatment and prevention of erectile dysfunction, vaginal dryness, benign prostatic hyperplasia and polycystic ovary syndrome.

18. The synthetic polypeptide sequence of claim 4, wherein heterologously expressed mechanosensitive channels, its variants, and the generated site-directed mutants thereof, optionally including bacterial mechanosensitive channels, plant mechanosensitive channels (MSL2-10), TRPV1-TRPV5 channels, Piezo channels or their generated site-directed mutants, for use as: osmoregulators, are activated by internal or external mechanical stimuli, and alternative outflow/inflow pathway for fluid in the treatment of any skin related diseases optionally including dysfunction of sweat glands; macromolecular pressure release valves, activated by internal or external mechanical stimuli, and alternative outflow pathway for fluid in the treatment of idiopathic intracranial hypertension; transmembrane ports in cells activated by internal or external mechanical stimuli for enhanced drug delivery in order to increase efficacy of the treatment for diseases including cancer; stimulation of cells, including neurons, cardiac and muscle cells for treatment and prevention diseases optionally including neurological diseases.

19. The synthetic polypeptide sequence of claim 4, where in the expression of said mechanosensitive channels, its variants, and the generated site-directed mutants thereof in cancer cells, are targeted by specific receptors optionally including EGFR, or pH environment, for use to precipitate cell death by either bioengineering a constitutively open a leaky channel or through overstimulation of the channel.

20. The protein of claim 4, wherein heterologously expressed mechanosensitive channels, its variants, and the generated site-directed mutants thereof, optionally including bacterial mechanosensitive channels, plant mechanosensitive channels (MSL2-10), TRPV1-TRPV5 channels, Piezo channels or their generated site-directed mutants, in neurons are activated by internal or external mechanical stimuli, for use in: modulating neural activities in order to repair injury optionally including concussion, enhance neural regeneration, accelerated learning and memory processing; or modulating activities in dormant neurons in order to recover from coma, and persistent vegetative state.

21. The synthetic polypeptide sequence of claim 4, wherein heterologously expressed mechanosensitive channels, its variants, and the generated site-directed mutants thereof, optionally including bacterial mechanosensitive channels, plant mechanosensitive channels (MSL2-10), TRPV1-TRPV5 channels, Piezo channels or their generated site-directed mutants, are activated by internal or external mechanical stimuli, for use as efflux ports for allowing the clearance of toxins from the central nervous system.

22. The synthetic polypeptide sequence of claim 4, wherein mechanosensitive channels, its variants, and the generated site-directed mutants thereof, optionally including bacterial mechanosensitive channels, plant mechanosensitive channels (MSL2-10), TRPV1-TRPV5 channels, Piezo channels or their generated site-directed mutants, heterologously expressed in Pneumocytes, are activated by internal or external mechanical stimuli, for use as ports for exchange of oxygen and Carbon dioxide from alveolus to the blood capillaries and vice a versa via the Pneumocytes in lung diseases optionally including but not limited to Black Lung Disease (Coal workers' pneumoconiosis).

23. The synthetic polypeptide sequence of claim 4, wherein the cells expressing the mechanosensitive channels, its variants, and the generated site-directed mutants thereof optionally including bacterial mechanosensitive channels, plant mechanosensitive channels (MSL2-10), TRPV1-TRPV5 channels, Piezo channels or their generated site-directed mutants, with or without fusion or conjugation of nanoprobes, are activated by a device providing external mechanical force or magnetic field, whose duration, frequency and strength is tunable for use in controlled stimulation, molecular delivery or cellular death leading to the desired therapeutic outcome.

24. The synthetic polypeptide sequence of claim 2, wherein at least one substitution is an I to L substitution at an amino acid residue corresponding to amino acid I at position 113 of SEQ ID NO: 1 which sensitizes sonic response activated by ultrasound.

25. The synthetic polypeptide sequence of claim 2, wherein at least one substitution is selected from:
- an A to H or C substitution at an amino acid residue corresponding to amino acid A at position 131 of SEQ ID NO: 1 to modulate the pore size of the channel to control the size of molecules that can be transported via the channels;
- an A to H or C substitution at an amino acid residue corresponding to amino acid A at position 133 of SEQ ID NO: 1 to modulate the size of a MscL1 nanovalve to control diffusion and active transport via said nanovalves;
- a G to any other 19 naturally occurring amino acid substitution at an amino acid residue corresponding to amino acid G at position 43 of SEQ ID NO: 1 leads to hypersensitivity to stretch forces that are activated at low threshold and an increase in pressure sensitivity;
- an I to any other 19 naturally occurring amino acid substitution at an amino acid residue corresponding to amino acid I at position 70 of SEQ ID NO: 1 in order to control MscL1 channel kinetics as well as mechanosensitivity;
- a V to C amino acid substitution at an amino acid residue corresponding to amino acid V at position 44 of SEQ ID NO: 1 to increase the pressure sensitivity and shorten open times compared to the polypeptide when no substitution is made at this position;
- a K to D or E amino acid substitution at an amino acid residue corresponding to amino acid K at position 52 of SEQ ID NO: 1 for increased pressure sensitivity and shortening mean open times and lowering a transition barrier compared to the polypeptide when no substitution is made at this position;
- a Q to C or P or F or W or Y or H amino acid substitution at an amino acid residue corresponding to amino acid Q at position 77 of SEQ ID NO: 1 for increased pressure sensitivity and shortening mean open times and lowering transition barrier compared to the polypeptide when no substitution is made at this position;
- an L to C amino acid substitution at an amino acid residue corresponding to amino acid L at position 40 of SEQ ID NO: 1 for increasing sensitivity to a higher gating threshold compared to the polypeptide when no substitution is made at this position;
- a K to any negatively charged amino acid substitution at an amino acid residue corresponding to amino acid K at position 122 of SEQ ID NO: 1 to tune the MscL1 channel mechanosensitivity and kinetics;

D to any amino acid substitution at an amino acid residue corresponding to amino acid D at 39 or position 42 of SEQ ID No. 1 for functional alterations; and
- a deletion of amino acid(s) from position(s) 131 to 133, 131 to 136 or 131 to 157 of SEQ ID NO: 1 for increasing the pressure sensitivity and shortening open times compared to the polypeptide when no deletions are made at these positions.

* * * * *